US011660126B1

(12) United States Patent
Abbasi et al.

(10) Patent No.: US 11,660,126 B1
(45) Date of Patent: May 30, 2023

(54) ILIAC ANCHOR SYSTEM

(71) Applicant: Advance Research System, LLC, Edina, MN (US)

(72) Inventors: Hamid R. Abbasi, Edina, MN (US); Kenneth R. Barra, Dallas, GA (US)

(73) Assignee: Advance Research System, LLC, Edina, MN (US)

( * ) Notice: Subject to any disclaimer, the term of this patent is extended or adjusted under 35 U.S.C. 154(b) by 0 days.

(21) Appl. No.: 16/915,463

(22) Filed: Jun. 29, 2020

Related U.S. Application Data

(60) Provisional application No. 62/884,469, filed on Aug. 8, 2019, provisional application No. 62/868,751, filed on Jun. 28, 2019.

(51) Int. Cl.
*A61B 17/70* (2006.01)

(52) U.S. Cl.
CPC ........ *A61B 17/704* (2013.01); *A61B 17/7055* (2013.01); *A61B 17/7083* (2013.01)

(58) Field of Classification Search
CPC ............ A61B 17/7055; A61B 17/7035; A61B 17/7037; A61B 17/704
USPC ........................................................ 606/266
See application file for complete search history.

(56) References Cited

U.S. PATENT DOCUMENTS

| | | | | |
|---|---|---|---|---|
| 5,254,118 A * | 10/1993 | Mirkovic | A61B 17/7041 606/264 |
| 6,981,973 B2 * | 1/2006 | McKinley | A61B 17/7037 606/264 |
| 8,052,726 B2 * | 11/2011 | Nayet | A61B 17/7038 606/278 |
| 9,055,980 B2 * | 6/2015 | Biedermann | A61B 17/7035 |
| 9,554,909 B2 * | 1/2017 | Donner | A61B 17/7076 |
| 10,070,895 B2 | 9/2018 | Barra et al. | |
| 10,646,260 B2 | 5/2020 | Abbasi | |
| 2003/0144666 A1 * | 7/2003 | Bagga | A61B 17/8033 606/279 |
| 2009/0287254 A1 * | 11/2009 | Nayet | A61B 17/7037 606/264 |
| 2014/0135839 A1 * | 5/2014 | Frankel | A61B 17/7043 606/264 |
| 2014/0249581 A1 * | 9/2014 | Stachniak | A61B 17/7044 606/264 |
| 2015/0012051 A1 | 1/2015 | Warrant et al. | |

* cited by examiner

*Primary Examiner* — Eduardo C Robert
*Assistant Examiner* — Christina Negrellirodriguez
(74) *Attorney, Agent, or Firm* — Christensen, Fonder, Dardi & Herbert PLLC; Stuart J. Olstad

(57) ABSTRACT

An anchoring system for a spinal support rod. The anchoring system includes a self-tapping orthopedic fastener that is bored through the ilium via a lateral incision and a mounting receiver that is positioned to receive the orthopedic fastener via a posterior incision. The orthopedic fastener may be implanted from a lateral approach or a posterolateral approach. The mounting receiver may be implanted from a posterior or superior posterior approach.

19 Claims, 16 Drawing Sheets

30, 30a
122
124
132
42
126
44
48
32, 32a
36
46
52
34, 34a
82
68
62
64
72, 75
74
108
32, 32b
102
92
94
96
104
106
66
112
114
116
128
134 z
Θ
r
78
33a
84
88
RO
31a
82
34,34a
62
72
33b
84
88
31b
34,34b
64
86
76

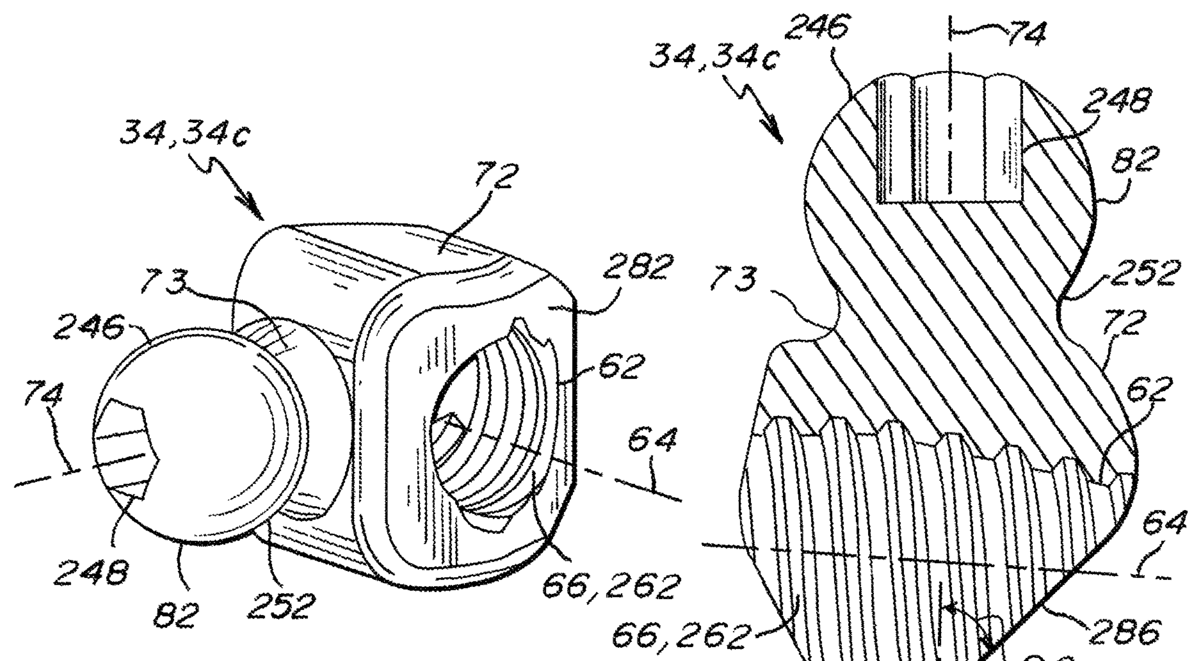
Fig.18
Fig.18A
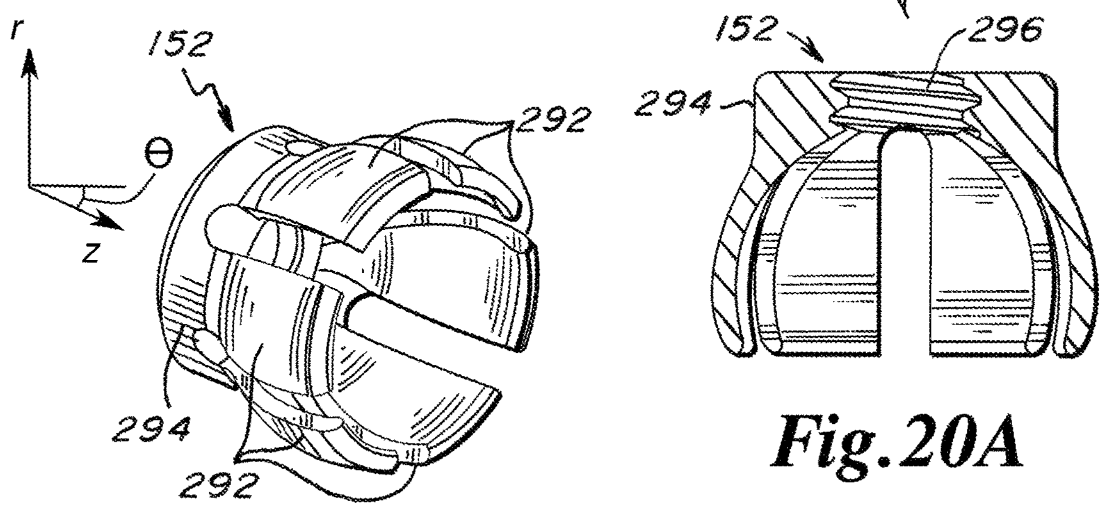
Fig.20
Fig.20A

ILIAC ANCHOR SYSTEM

RELATED APPLICATIONS

This patent application claims the benefit of U.S. Provisional Application No. 62/868,751, filed Jun. 28, 2019, and of U.S. Provisional Patent Application No. 62/884,469, filed Aug. 8, 2019, the disclosures of which are hereby incorporated by reference herein in their entireties.

FIELD OF THE DISCLOSURE

This patent application is directed generally to spinal support systems and more specifically to anchoring of spinal support systems.

BACKGROUND

Implementation of various spinal surgical techniques often require the use of spinal support rods that are anchored to the vertebrae with pedicle screws to provide stabilization of the spine during treatment of spinal disorders. Examples include application of a coercive force to the spine for corrective purposes (e.g., correction of scoliosis). Another example is maintaining adjacent vertebrae stationary so that bone growth tissue can bridge the vertebrae in a spinal fusion process. Such spinal support systems may be subject to substantial anchoring forces to accomplish the prescribed support or corrective action. An orthopedic anchoring system having enhanced strength characteristics to maintain the integrity of the spinal support system while enabling greater forces to be exerted thereon would be welcomed.

SUMMARY OF THE DISCLOSURE

Various embodiments of the disclosure provide an orthopedic anchoring system with structural and mounting characteristics that enhances strength and integrity by several factors and resulting in reduced failure rates relative to conventional anchoring systems, The orthopedic anchoring system is mounted to the ilium proximate the iliac crest, where there are fewer ligaments and nerves relative to other regions of the lower spine, thereby providing for a safer and less problematic implant. The implant may be performed either as an alternative to or in addition to standard pedicle screw mounts at the L5 or S1 vertebrae. The implantation may be performed using minimally invasive techniques in a matter of a few minutes, with attendant faster recuperation rates.

Conventional spinal support systems include spinal support rod is anchored to the lower portions of the spine, such as at the L5 or S1 vertebrae, with pedicle screw anchors. Certain applications require substantial forces, for example for fusion of multiple vertebrae. The forces that pedicle screws can accommodate can be limiting. Most failures of such conventional spinal support systems result from failure of the pedicle screw anchor. Some spinal support systems attempt to enhance the anchoring strength by increasing the length of the anchoring pedicle screw anchor. But lengthening the pedicle screw anchor provides limited benefit, and the the increased length can be difficult or risky to implement in the regions at the base of the spine, where nerves and ligaments are ubiquitous. Furthermore, there are instances where the base of the spine of a given patient is not suitable to accommodate a pedicle screw anchor, for example where the lower portions of the spine have been subjected to trauma.

The disclosed anchoring system addresses these limitations and shortcomings of conventional spinal support systems. Structurally, an anchoring system for a spinal support assembly is disclosed, comprising an orthopedic fastener including a proximal end portion, a mid-portion, and a threaded distal end portion arranged along a central axis. A mounting receiver is configured to engage the threaded distal end portion along a receiver axis, the central axis and the receiver axis being concentric when the orthopedic fastener and the mounting receiver are engaged. A support rod receptacle is coupled to the standoff of the mounting receiver, the support rod receptacle extending radially outward from the receiver axis. In some embodiments, a standoff extends radially outward from the receiver axis, the support rod receptacle being coupled to the standoff, and may include a ball pivot, the support rod receptacle being configured to receive the ball pivot to define a polyaxial connection. In some embodiments, the mounting receiver and the support rod receptacle are unitary. In some embodiments, the mounting receiver defines a wedge shape. In some embodiments, the mounting receiver defines a concave face for seating the mounting receiver against a bone, for example, by defining opposed lateral edges that seat the mounting receiver.

In some embodiments, the proximal end portion of the orthopedic fastener includes a head portion, which may include a flange having a distal face that includes a radiused shoulder, a bottom-tapped hole accessible from a proximal face of the head portion, and/or wherein the proximal end portion defines a first polygonal socket that extends distal to and is accessible from bottom tapped hole. Some embodiments include a profiled washer that surrounds the proximal end portion of the orthopedic fastener, and may also include a head portion at the proximal end portion, the head portion being configured to engage a concave face of the profiled washer. In some embodiments, the concave face of the profiled washer defines a spherical profile, and the head portion defines a convex spherical profile that interfaces with the concave spherical profile of the profiled washer. Some embodiments comprise a guide tower frangibly connected to the support rod receptacle.

In various embodiments of the disclosure, a method for anchoring a spinal support system in a patient is disclosed, comprising providing a kit including an orthopedic anchoring system, the orthopedic anchoring system including an orthopedic fastener, a mounting receiver, and a support rod receptacle and providing instructions for implanting the orthopedic anchoring system. The instructions include: positioning the mounting receiver on an ilium and proximate an iliac crest of a patient; passing the orthopedic fastener through the ilium; and coupling the orthopedic fastener to the mounting receiver. In some embodiments, the kit additionally includes one or more of a guide tower, a tool, a driver assembly, a pilot hole drill, and a guide wire. In some embodiments, the instructions provide that the step of passing the orthopedic fastener through the ilium comprises passing the orthopedic fastener through the ilium from one of a lateral approach and a posterolateral approach. In some embodiments, the instructions provide that the step of positioning the mounting receiver on the ilium in the instructions provided in the step of providing instructions comprises positioning the mounting receiver on the ilium from a superior posterior approach.

In various embodiments of the disclosure, a system for securing a mounting receiver assembly to an ilium bone is disclosed, comprising: an orthopedic fastener defining a central rotational axis and having a proximal end portion, a mid-portion, and a distal end portion that are concentric about the central rotational axis, the orthopedic fastener defining a central through-passage concentric about the central rotational axis that passes through the proximal end portion, the mid-portion, and the distal end portion; a mounting receiver defining a mounting aperture for coupling to the distal end portion of the orthopedic fastener, the mounting aperture defining and extending along a mounting axis; and a draw rod disposed in the central through-passage. In this embodiment: the mounting aperture of the mounting receiver includes female threads; the distal end portion of the orthopedic fastener includes a male threaded section configured to engage the female threads of the mounting aperture, the distal end portion defining at least one axially extending slot that radially and tangentially bifurcates the male threaded section so that the male threaded section defines a plurality of axially extending segments; the mid-portion includes external bone-engaging threads configured to engage bone tissue; and the draw rod includes a mandrel portion at a distal end, the mandrel portion being distal to the distal end portion of the orthopedic fastener when the orthopedic fastener and the mounting receiver assembly are in an unlocked configuration, the mandrel portion being disposed at least partially within the plurality of axially extending segments when the orthopedic fastener and the mounting receiver assembly are in a locked configuration. In some embodiments, the draw rod includes male threads, and the central through-passage of the orthopedic fastener includes female threads, the male threads of the draw rod being configured to threadably engage with the female threads of the central through-passage. The male threads of the draw rod may be proximate a proximal end thereof, and the female threads of the central through-passage are at the proximal end portion of the orthopedic fastener.

BRIEF DESCRIPTION OF THE DRAWINGS

FIG. 18 is a perspective view of a mounting receiver for an anchoring system of FIG. 13 according to an embodiment of the disclosure;

FIG. 18A is a sectional view of the mounting receiver of FIG. 18 according to an embodiment of the disclosure;

FIG. 20 is a perspective view of a ball retainer for the anchoring system of FIG. 13 according to an embodiment of the disclosure;

FIG. 20A is a sectional view of the ball retainer of FIG. 20 according to an embodiment of the disclosure;

DETAILED DESCRIPTION OF THE DRAWINGS

Figure 1:
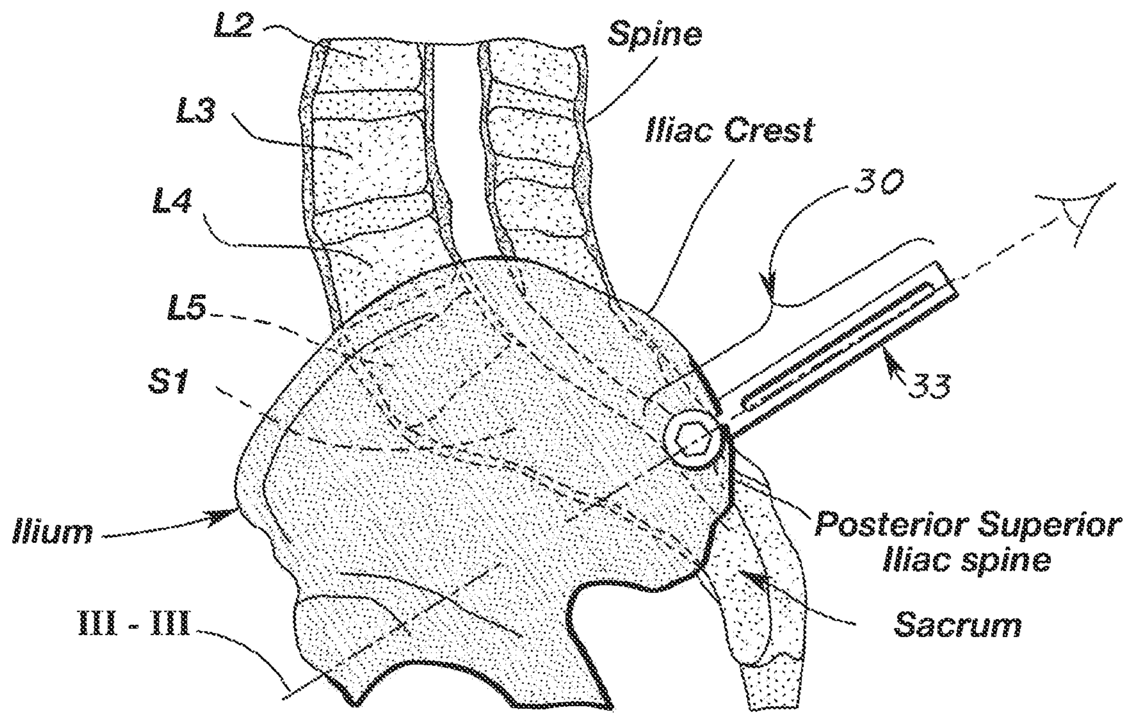
FIG. 1 is a lateral view of a lower spine and ilium with an orthopedic anchoring system implanted therein according to an embodiment of the disclosure
Figure 2:
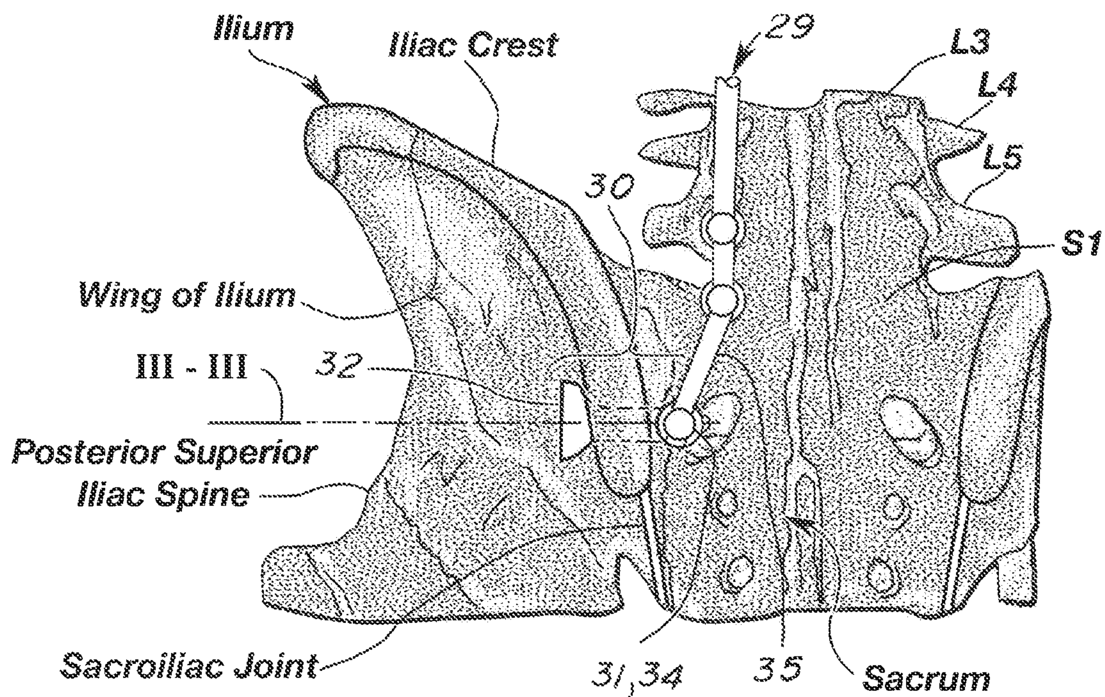
FIG. 2 is a partial superior posterior view of the implanted orthopedic anchoring system of FIG. 1 parallel to plane according to an embodiment of the disclosure.
Figure 3:
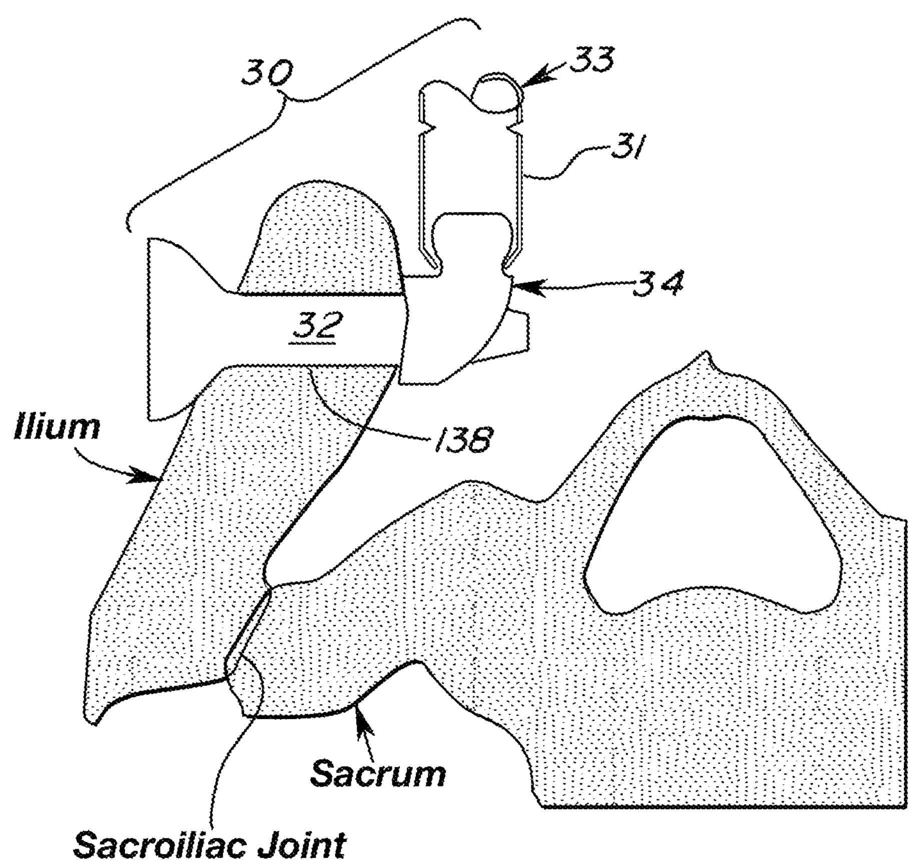
FIG. 3 is an axial, sectional view of the implanted orthopedic anchoring system of FIG. 1 orthogonal to plane according to an embodiment of the disclosure.

Referring to FIGS. 1 through 3, an orthopedic anchoring system 30 implanted in an ilium for anchoring a spinal support assembly 29 is depicted according to an embodiment of the disclosure. The orthopedic anchoring system 30 includes an orthopedic fastener 32 coupled to a receiver assembly 33. The receiver assembly 33 includes a mounting receiver 34 coupled to a support rod receptacle or "tulip" 31 for receiving a spinal support rod 35. The "tulip" moniker is recognized in the spinal support arts as the support rod receptacle. Structural aspects of the tulip 31 are detailed, for example, at U.S. Pat. No. 10,646,260 to Abbasi, owned by the owner of the present application, the content of which is hereby incorporated by reference herein in its entirety except for express definitions and patent claims contained therein. The orthopedic anchoring system is coupled to the implanted spinal support assembly 29 via the spinal support rod 35, acting as an anchor for maintaining therapeutic forces on the assembly 29. For the depicted embodiment, the orthopedic fastener 32 is mounted to the ilium proximate the iliac crest, and the receiver assembly 33 oriented on a superior posterior plane III-III Referring to FIGS. 4 through 12, orthopedic anchoring systems 30*a* and 30*b* are depicted according to an embodiment of the disclosure. Herein, the orthopedic anchoring systems, tulips, orthopedic fasteners, receiver assemblies, and mounting receivers are referred to generically or collectively with reference characters 30, 31, 32, 33, and 34, respectively, and specific or individual orthopedic anchoring systems and associated components are designated with a letter suffix (e.g., "orthopedic anchoring system 30*c* including orthopedic fastener 32*d* and receiver assembly 33*c* with mounting receiver 34*c* with tulip 31*b*"). In view of this disclosure, an artisan of ordinary skill will recognize that the tulips 31, orthopedic fasteners 32, and mounting receivers 34 are generally interchangeable, so that hybrid anchoring systems 30 and receiver assemblies 33 may be configured that are not specifically depicted herein. Such hybrid anchoring systems 30 and receiver assemblies 33 are within the scope of this disclosure. That is, the orthopedic anchoring systems 30 and receiver assemblies 33 depicted herein are not limiting.

Figure 14:
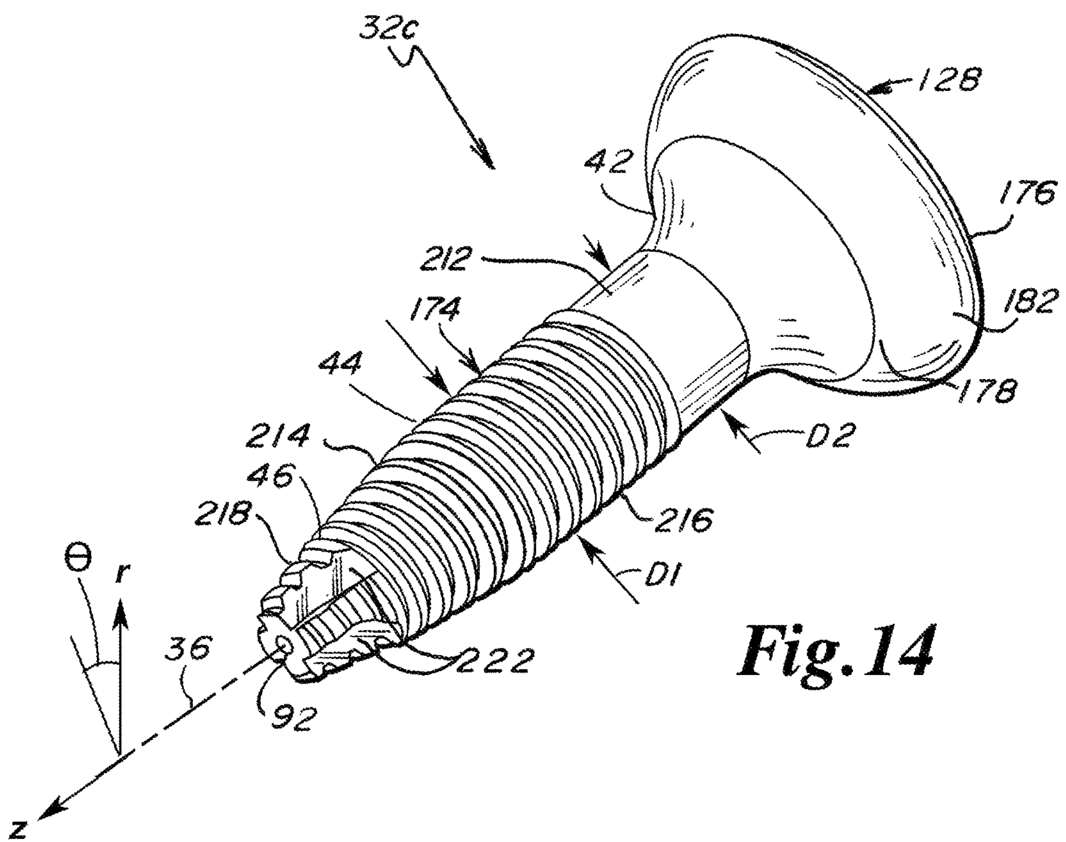
FIG. 14 is a perspective view of an orthopedic fastener for the anchoring system of FIG. 13 according to an embodiment of the disclosure.
Figure 14A:
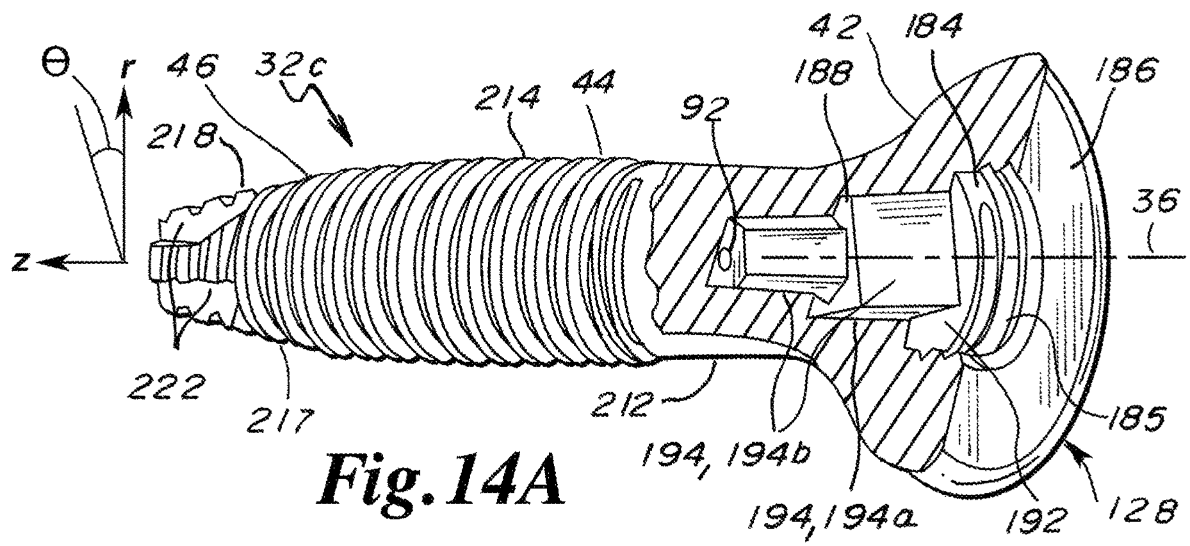
FIG. 14A is a perspective, partial cutaway view of the orthopedic fastener of FIG. 14 according to an embodiment of the disclosure.

Each orthopedic fastener 32 defines a central rotational axis 36 about which the fastener 32 is rotated and includes a proximal end portion 42, a mid-portion 44, and a distal end portion 46 that are concentric about the axis 36. The mid-portion 44 of the orthopedic fasteners 32*a* and 32*b* includes external threads 48 configured to engage bone tissue. The distal end portion 46 of the orthopedic fasteners 32*a* and 32*b* includes a male threaded section 52 and may include self-tapping features, such as depicted at FIG. 14. In some embodiments, a diameter of the external threads 48 is greater than a diameter of the threads of the male threaded section 52.

Each mounting receiver 34 includes a receiver body 72, a standoff 73, and the tulip 31. The standoff 73 extends radially outward from a receiver or mounting axis 64 along a standoff axis 74. For receiver assemblies 33*a* and 33*b* and associated mounting receivers 34*a* and 34*b*, the receiver body 72 is a flange 75. The receiver body 72 defines a mounting aperture 62 concentric about the mounting axis 64 for coupling to the distal end portion 46 of the orthopedic fastener 32, the mounting aperture 62 defining and extending along the mounting axis 64. In some embodiments, the mounting aperture 62 includes female threads 66. The female threads 66 of the mounting receiver 34 are configured to threadably engage the male threaded section 52 at the distal end portion 46 of the orthopedic fastener 32.

The tulip 31 includes female threads 76 concentric about a tulip axis 78, the tulip 31 defining an outer radius RO about the tulip axis 78. In some embodiments, the receiver assembly 33 includes a removable guide tower 84 (FIG. 11) that extends from the tulip 31 for guiding a set screw 86 along the tulip axis 78 and into the tulip 31. The guide tower 84 may be configured to slidingly guide the set screw 86 toward the tulip 31, to threadably guide the set screw 86 toward the tulip 31, or a combination of slidingly and threadably guiding the set screw 86 toward the tulip 31. The guide tower 84 may be coupled to the tulip 31 with a frangible connection 88 (i.e., a connection that is easily broken). For the orthopedic anchoring system 30*a*, the standoff 73 is rigidly attached to a tulip 31*a*. For the orthopedic anchoring system 30*b*, the standoff 73 includes a ball pivot 82 for polyaxial connection to a tulip 31*b*.

In some embodiments, the orthopedic fastener 32 defines a central through-passage 92 concentric about the central axis 36 that passes through the proximal end portion 42, the mid-portion 44, and the distal end portion 46 of the orthopedic fastener 32. The distal end portion 46 may define at least one axially extending slot 94 that radially and tangentially bifurcates the male threaded section 52, as depicted for the orthopedic fastener 32*b*. Herein, "tangential" and its derivatives refer to a direction along the θ-coordinate of an r-θ-z coordinate system; "radial" or "lateral" refer to a direction along or parallel to the r-coordinate, and "axial" refers to a direction along or parallel to the z-coordinate. The bifurcation of the male threaded section 52 defines a plurality of axially extending segments 96. In some embodiments, the plurality of segments 96 is four segments 96 (depicted).

In some embodiments, a draw rod 102 is disposed in the central through-passage 92, such as depicted for the orthopedic anchoring system 30*b*. The draw rod 102 may include a mandrel portion 104 at a distal end 106 thereof, the mandrel portion 104 being distal to the distal end portion 46 of the orthopedic fastener 32*b* when the orthopedic fastener 32*b* and the mounting receiver 34*b* are in an unlocked configuration 108. In a locked configuration, the mandrel portion 104 is seated at least partially within the plurality of segments 96. In some embodiments, the draw rod 102 includes male threads 112, and the central through-passage 92 of the orthopedic fastener 32*b* includes female threads 114, the male threads 112 of the draw rod 102 being configured to threadably engage with the female threads 114 of the central through-passage 92. The male threads 112 of the draw rod 102 may be proximate a proximal end 116 of the draw rod 102, with the female threads 114 of the central through-passage 92 being proximate the proximal end portion 42 of the orthopedic fastener 32*b*.

In some embodiments, the orthopedic anchoring system 30 includes a nut 122 including female threads 124, as depicted for the orthopedic anchoring system 30*a*. The orthopedic fastener 32*a* includes male threads 126 at the proximal end portion 42 configured to threadably engage the female threads 124 of the nut 122. In other embodiments, the orthopedic fastener 32 includes a head portion 128 at the proximal end portion 42, such as depicted for orthopedic anchoring system 30*b*. In some embodiments, the orthopedic anchoring system 30 includes a washer 132 against which the nut 122 or the head portion 128 register when the orthopedic anchoring system 30 is implanted. The proximal end portion 42 of the orthopedic fastener 32 may define a counter bore 134 for access to the proximal end 116 of the draw rod 102, as depicted for the orthopedic fastener 32*b*.

Figures 4, 5:
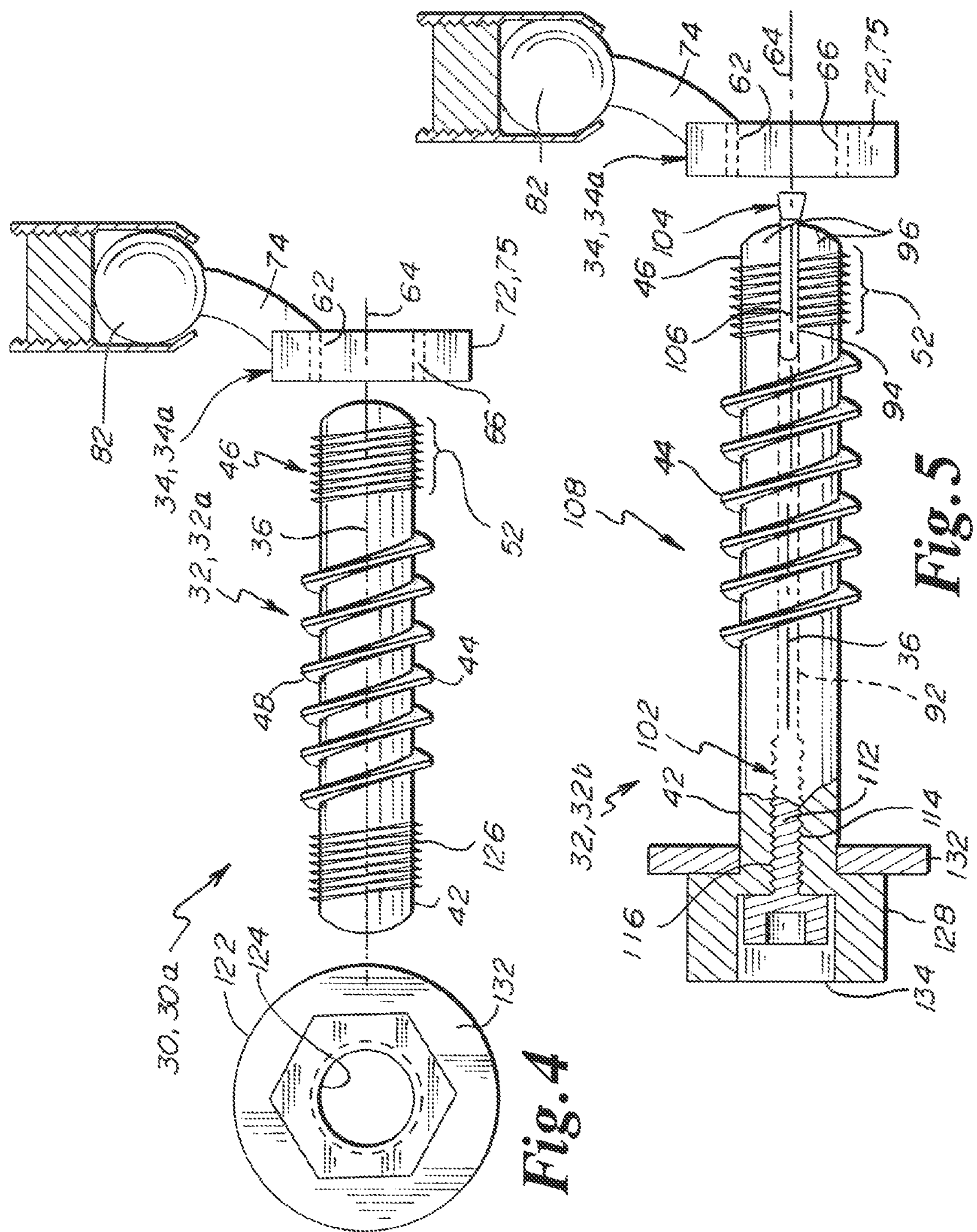
FIG. 4 is a side view of an iliac anchoring system according to an embodiment of the disclosure.
FIG. 5 is a side view of an iliac anchoring system according to an embodiment of the disclosure.
Figure 6:
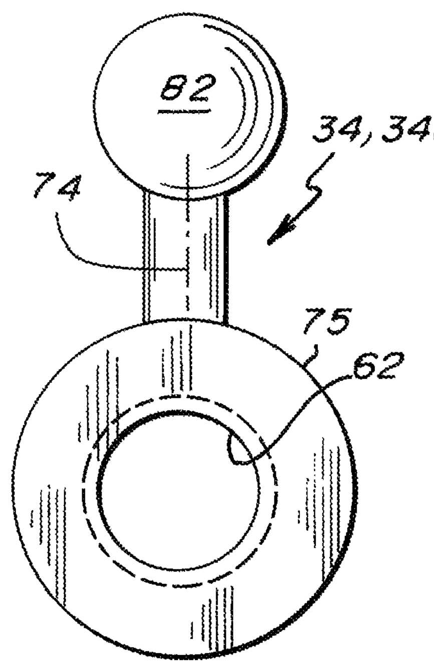
FIG. 6 is an elevational view of a mounting receiver for the anchoring systems of FIGS. 4 and 5 according to embodiments of the disclosure.
Figure 7:
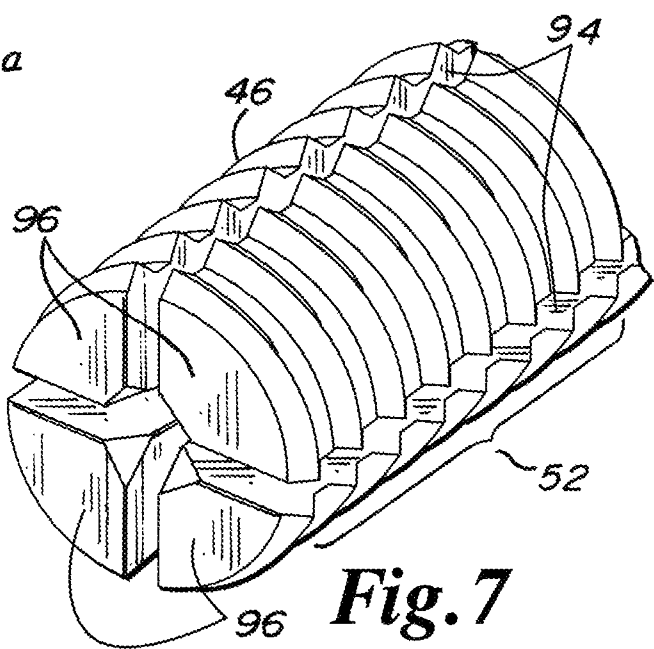
FIG. 7 is an enlarged perspective view of a distal end portion of an orthopedic fastener having a plurality of axially extending segments according to an embodiment of the disclosure.
Figure 8:
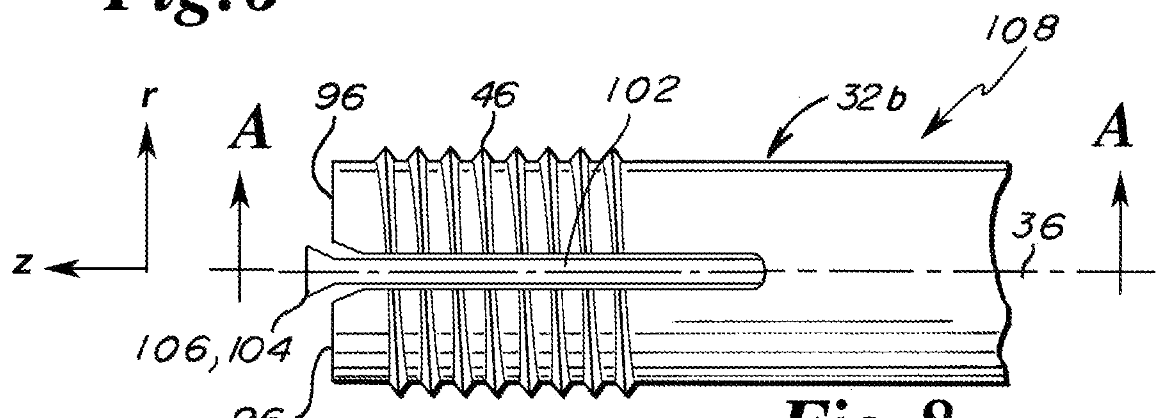
FIG. 8 is an enlarged side view of the distal end portion of FIG. 7 with a draw rod installed according to an embodiment of the disclosure.
Figure 8A:
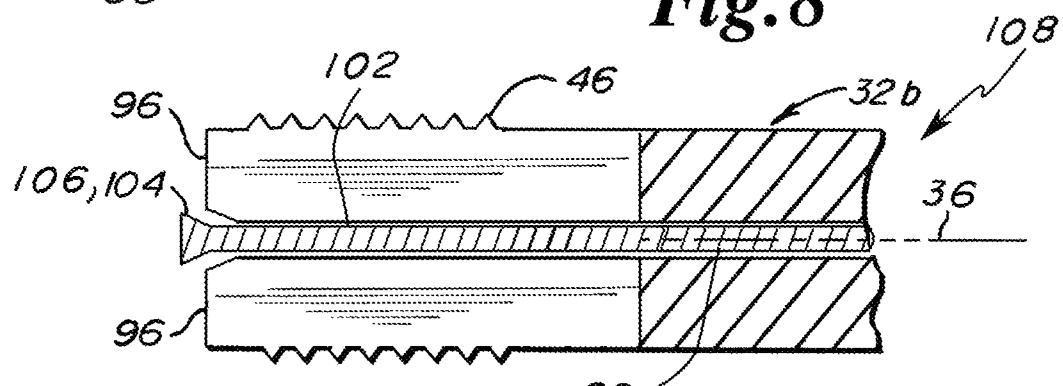
FIG. 8A is a sectional view along plane A-A of FIG. 8 according to an embodiment of the disclosure.
Figures 9, 10, 11, 12:
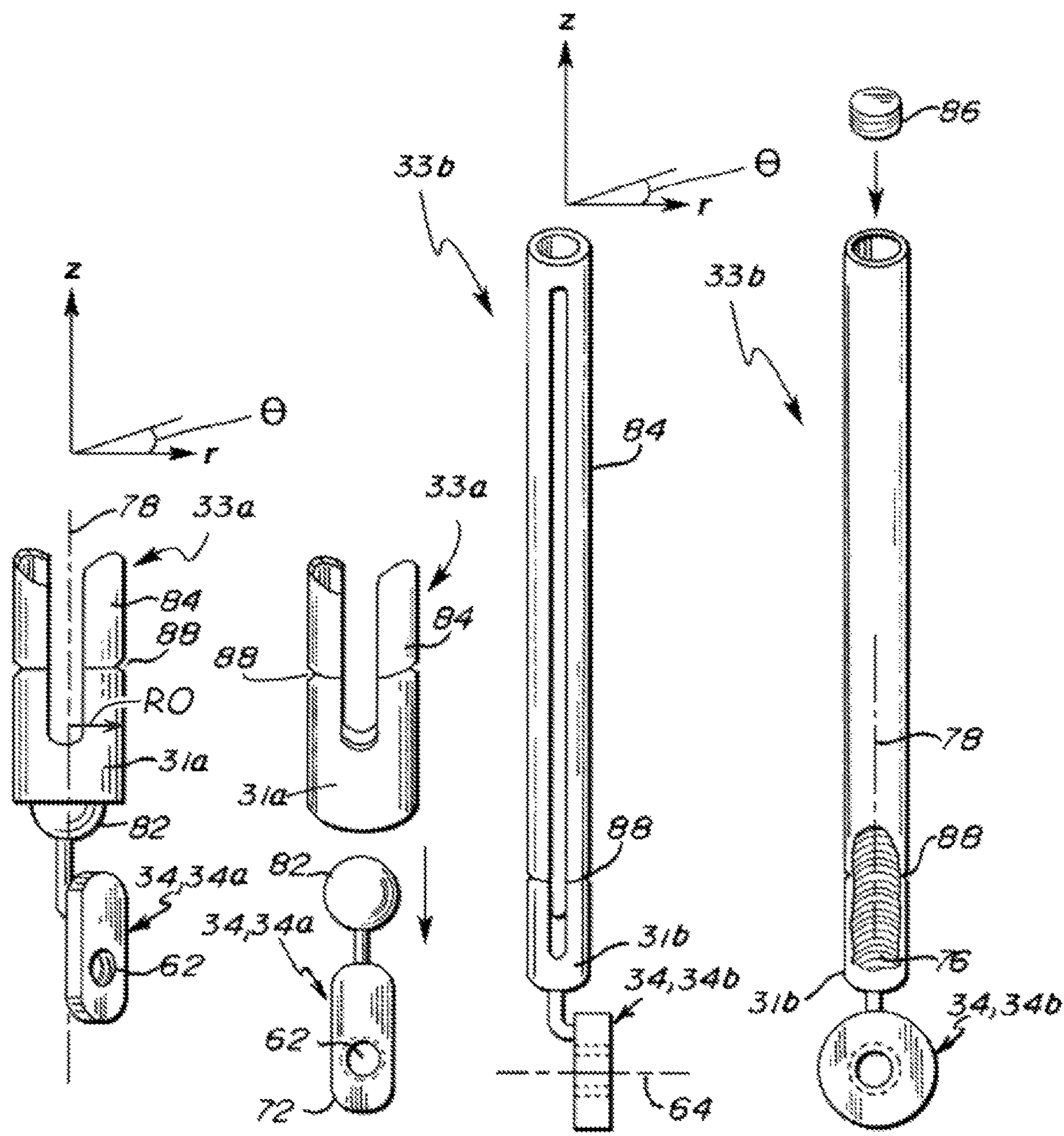
FIG. 9 is a partial perspective view of a receiver and tulip in a polyaxial arrangement according to an embodiment of the disclosure.
FIG. 10 is an exploded view of the receiver and tulip arrangement of FIG. 11 according to an embodiment of the disclosure.
FIG. 11 is a first side elevational view of a receiver and tulip combination according to an embodiment of the disclosure.
FIG. 12 is a second side elevational cutaway view of the receiver and tulip combination of FIG. 9 according to an embodiment of the disclosure.

For operation of anchoring systems 30*a* and 30*b*, as well as for anchoring systems 30 generally, a bore 138 is formed in the ilium (FIG. 3). For orthopedic fasteners 32 that implement the self-tapping features, the bore 138 is formed with the orthopedic fastener 32, without need for pre-drilling the bore 138. The external threads 48 are screwed into the bone surrounding the bore 138, which may be facilitated by the larger diameter of the external threads 48. With the receiver assembly 33 held in place, the orthopedic fastener 32 is threaded through the ilium so that the male threaded section 52 of the distal end portion 46 protrudes through the ilium and into mounting aperture 62 of the mounting receiver 34. The mounting receiver 34 is drawn against the ilium by the advancement of the orthopedic fastener 32 into the mounting receiver 34. The orthopedic fastener 32 is drawn into tension, for example by the nut 122 of orthopedic fastener 32*a* (FIG. 4) or the head portion 128 of orthopedic fastener 32*b* (FIG. 5).

For the orthopedic anchoring system 30*b*, after setting the orthopedic fastener 32*b* within the ilium and drawing the mounting receiver 34*b* tightly against the ilium, the draw rod 102 is drawn proximally through the orthopedic fastener 32*b*, for example rotationally, utilizing the threads 112 and 114. As the mandrel portion 104 of the draw rod 102 is proximally drawn into the orthopedic fastener 32*b*, the axially extending segments 96 are splayed radially outward, which expands the male threaded section 52 radially outward to bind the male threads of the threaded section 52 within the female threads 66 of the mounting receiver 34*b*. In this way, the mounting receiver 34*b* is rotationally fixed and locked with respect to the orthopedic fastener 32*b*.

Figure 13:
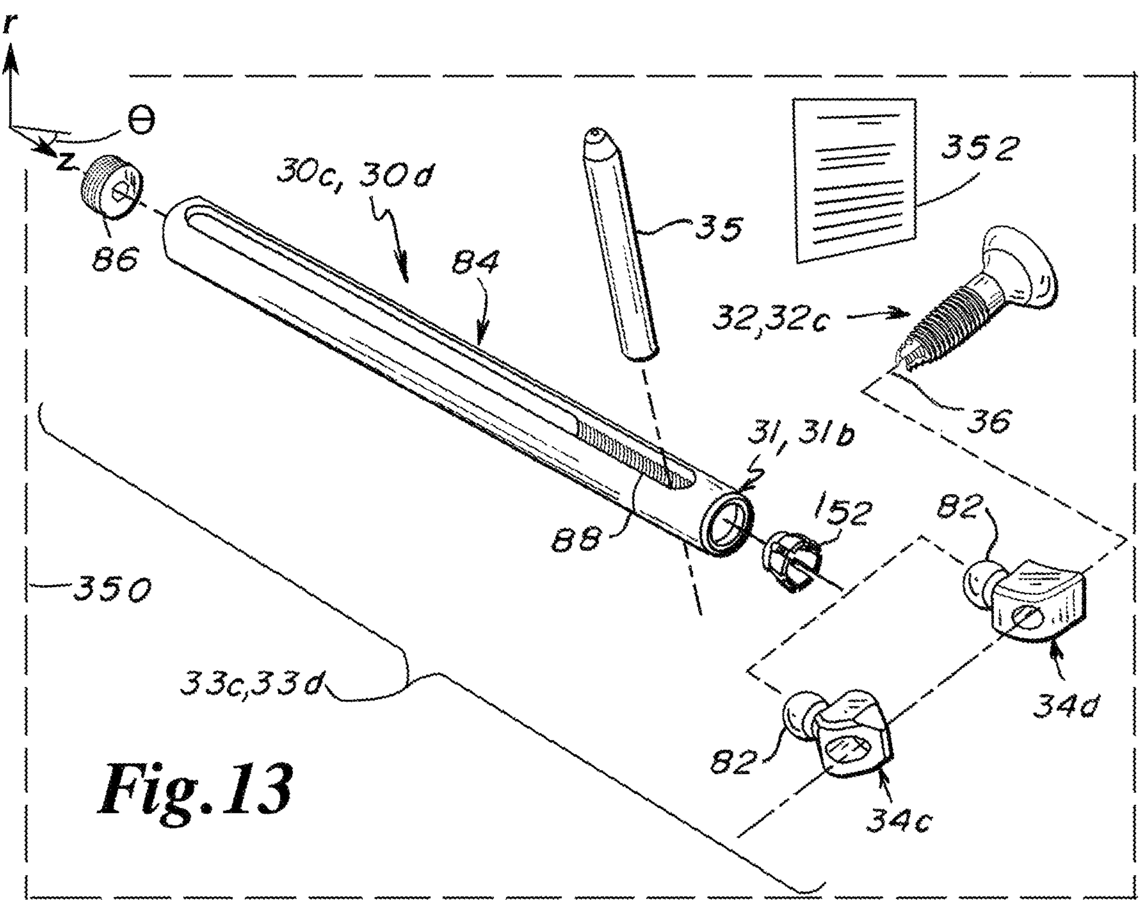
FIG. 13 is an exploded view of alternative anchoring systems according to embodiments of the disclosure.

Referring to FIG. 13, orthopedic anchoring systems 30*c* and 30*d* are depicted according to embodiments of the disclosure. The orthopedic anchoring systems 30*c*, 30*d* include a receiver assembly 33*c* or 33*d* comprising the tulip 31*b* and one of a mounting receiver 34*c* or 34*d*. As depicted, the orthopedic anchoring systems 30*c*, 30*d* include an orthopedic fastener 32*c*; however, any of the orthopedic fasteners 32*c*, 32*d*, or 32*e* (detailed below) may be implemented with the orthopedic anchoring systems 30*c*, 30*d*. In the depicted embodiment, the orthopedic anchoring systems 30*c*, 30*d* include the guide tower 84, the set screw 86, and the ball pivot 82 for polyaxial connection to the tulip 31*b*. In addition, the orthopedic anchoring system 30*c* may include a ball retainer 152. A portion of the spinal support rod 35 is also represented in line for insertion into the tulip 31*b*.

Figure 14B:
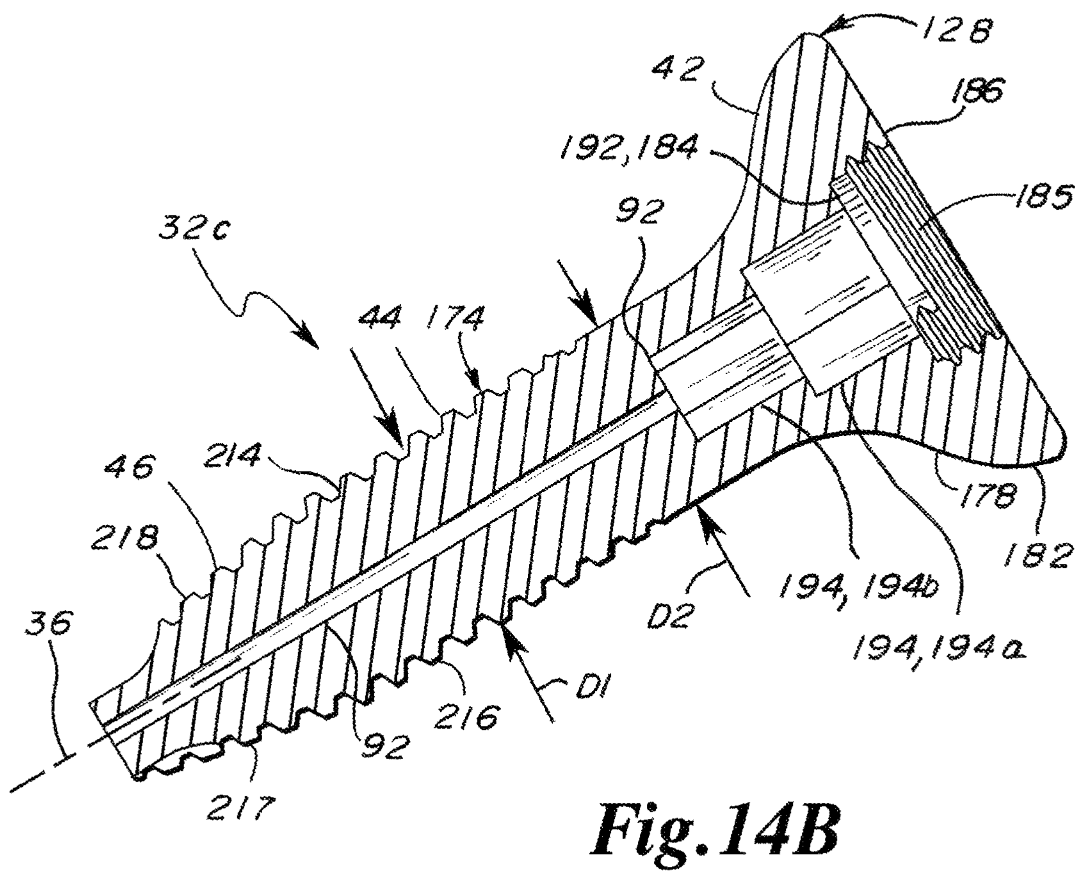
FIG. 14B is a sectional view of the orthopedic fastener of FIG. 14 according to an embodiment of the disclosure.

Referring to FIGS. 14 through 14B, the orthopedic fastener 32*c* is depicted in greater detail according to an embodiment of the disclosure. The orthopedic fastener 32*c* may include some of the same components and attributes as orthopedic fasteners 32*a* and 32*b*, some of which are indicated with same-labeled reference characters. The orthopedic fastener 32*c* includes the head portion 128 and a shaft portion 174 that extends distally from the head portion 128. The head portion may include a flange 176 with a distal face 178 having a radiused shoulder 182. In some embodiments, the head portion 128 defines a bottom-tapped hole 184 accessible from a proximal face 186, the bottom-tapped hole 184 defining threads 185. In some embodiments, a cavity 188 extends into the shaft portion 174 from a distal extremity 192 of the bottom-tapped hole 184. The cavity 188 may define sequential sockets 194, including a proximal socket 194*a* and a distal socket 194*b*, each defining a unique polygonal shape. In the depicted embodiment, the proximal socket 194*a* defines a square-shaped polygon, and the distal socket 194*b* defines a hexagonal-shaped polygon. The orthopedic fastener 32, 32*c* may also define the central through-passage 92 that extends through the orthopedic fastener 32, 32*c*, concentric about the central rotation axis 36.

The shaft portion 174 of the orthopedic fastener 32*c* may include a proximal shank portion 212 and threaded distal portion 214. In some embodiments, a crest 216 of the threaded distal portion 214 defines a maximum first diameter D1 and the proximal shank portion 212 defines a second diameter D2, the maximum first diameter D1 being greater than the second diameter D2. The threaded portion 214 may define male threads 217 at a tapered distal tip portion 218. In some embodiments, one or more self-tapping flutes 222 are defined at the tapered distal tip portion 218.

Figure 15:
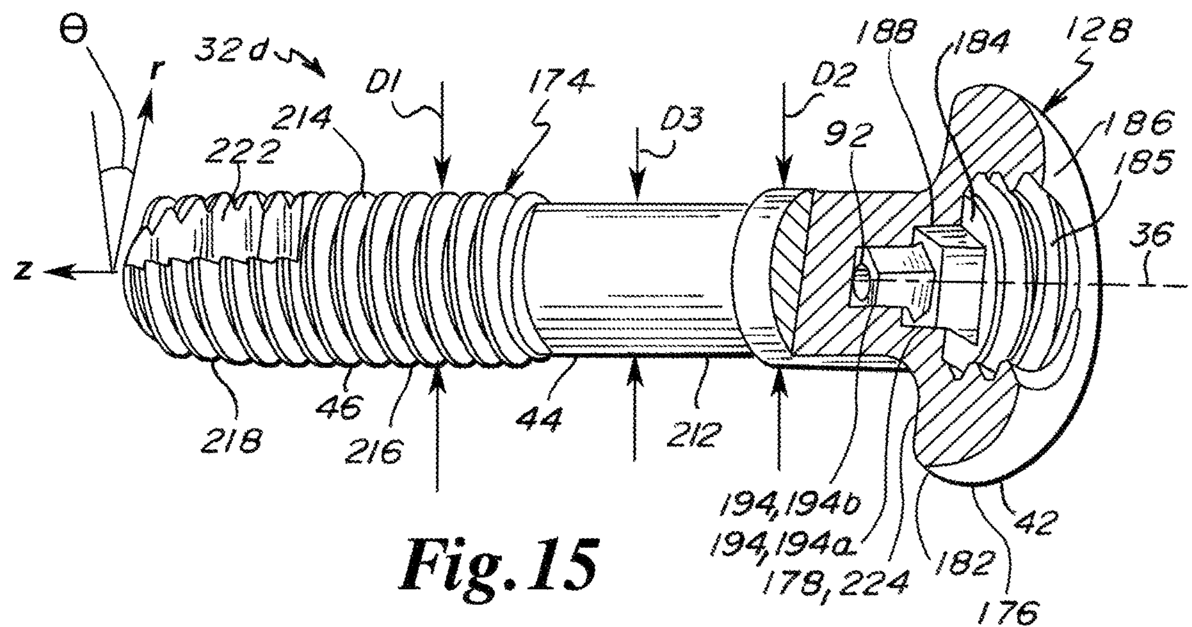
FIG. 15 is a perspective, partial cutaway view of an alternative orthopedic fastener for use with the anchoring system of FIG. 13 according to an embodiment of the disclosure.

Referring to FIG. 15, an orthopedic fastener 32*d* is depicted according to an embodiment of the disclosure. The orthopedic fastener 32*d* includes many of the same components and attributes as orthopedic fastener 32*c*, some of which are indicated by same-labeled reference characters. The orthopedic fastener 32*d* presents a flat 224 on the distal face 178 of the head portion 128, the flat 224 being substantially orthogonal to the central rotation axis 36. In some embodiments, the orthopedic fastener 32*d* includes a reduced diameter D3 at the mid-portion 44, the reduced diameter D3 being reduced relative to the maximum first diameter D1 and the second diameter D2.

Functionally, the flat 224 enables the orthopedic fastener 32*d* seat on cortical bone surface with limited disturbance to the opening of the bore 138 that is formed by the implantation. The flat 224 also enables various washers and washer assemblies (e.g., washer 132 of FIG. 5) to be incorporated into the associated orthopedic anchoring system 30. The reduced diameter D3 can, in some embodiments, enable the orthopedic fastener 32*d* to rotate freely within the bore 138 formed by the fastener 32*d*. The free rotation enables easier rotational orientation of the associated receiver assembly 33 about the axes 36, 64 of the orthopedic anchoring system 30 as the orthopedic fastener 32*d* and receiver assembly 33 are drawn together. The reduced diameter D3 may also be implemented with orthopedic fastener 32*c*.

Figure 16:
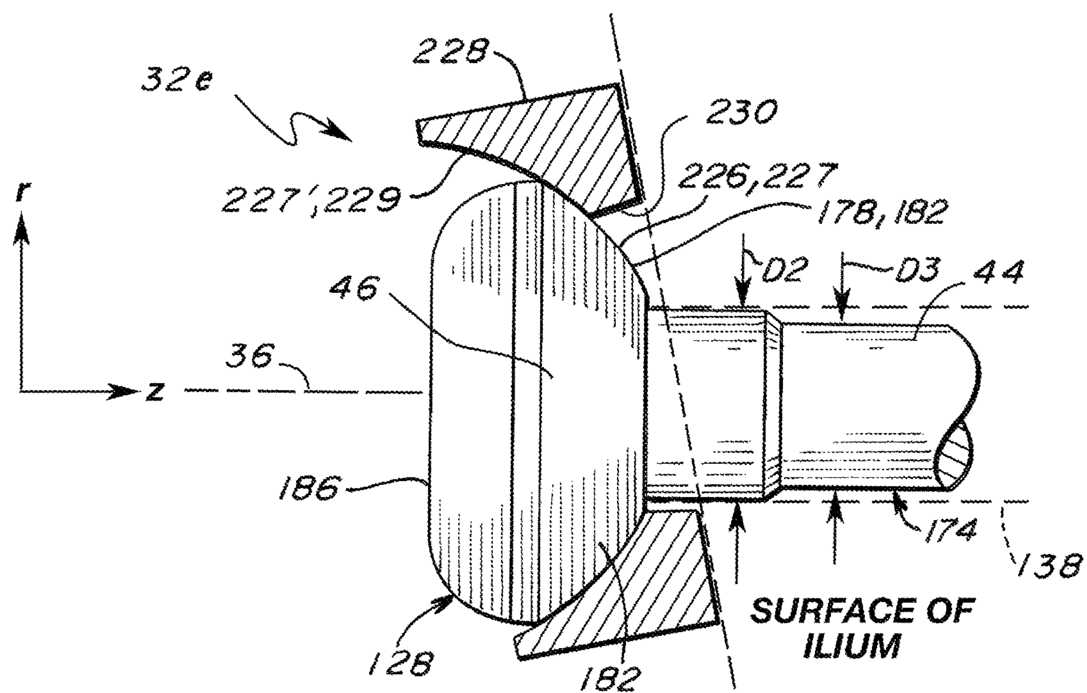
FIG. 16 is a perspective, partial view of an alternative orthopedic fastener with a profiled washer for use with the anchoring system of FIG. 13 according to an embodiment of the disclosure.

Referring to FIG. 16, the proximal of an orthopedic fastener 32*e* with a profiled washer 228 is depicted according to an embodiment of the disclosure. The orthopedic fastener 32*e* includes many of the same components and attributes as orthopedic fastener 32*d*, some of which are indicated by same-labeled reference characters. The distal face 178 of the head 128 of the orthopedic fastener 32*e* includes a convex surface 226, presenting, for example a spherical profile 227. The profiled washer 228 includes a concave surface 229, presenting, for example a spherical profile 227'. The profiled washer 228 may define an oversized through-aperture 230 that is oversized with respect to the second diameter D2 of the orthopedic fastener 32*e*. When implanted, the profiled washer 228 is captured between the head 128 and the surface of the ilium and engages the convex surface 227 of the distal face 178.

Functionally, the orthopedic fastener 32*e* and profiled washer 228 combination can accommodate seating on a bone (ilium) surface that is not orthogonal to axis of the bore 138, thereby providing a more uniform seating on the bone surface. The alignment causes the profiled washer 228 to seat substantially normal to the surface of the cortical bone with limited disturbance to the opening of bore 138. The profiled washer 228 may distribute the clamping force of the orthopedic anchoring system 30 more evenly and over a larger area than would the head 128, and may prevent sliding (abrasive) contact on the bone surface as the orthopedic fastener 32 is rotationally threaded into place.

Figure 28:
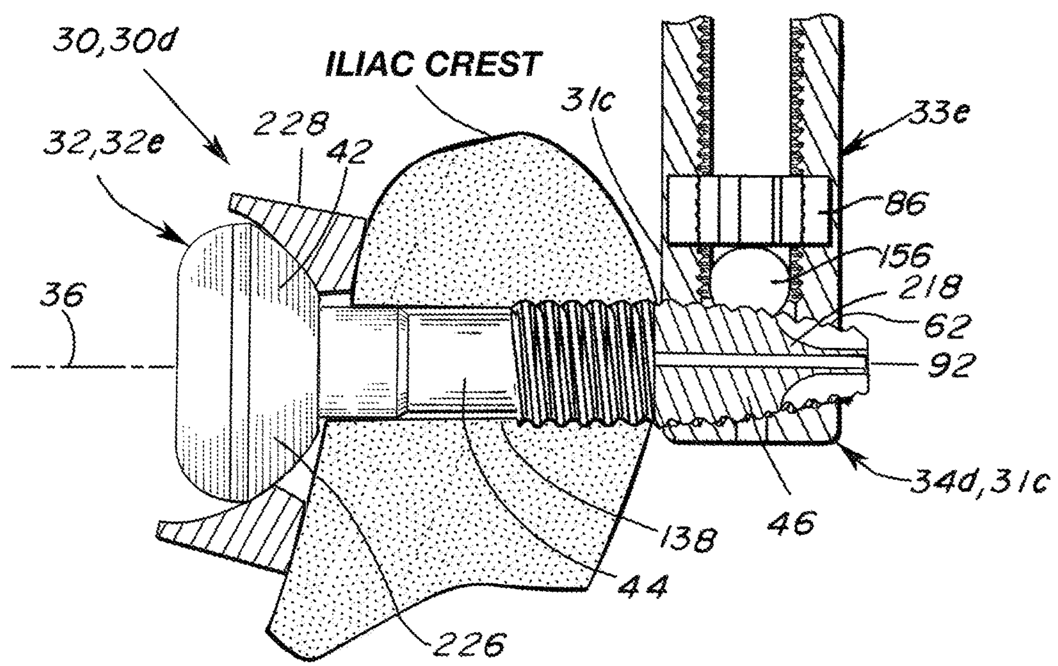

The oversized through-aperture 230 enables compliance over a range of angles. The convex and concave surfaces 227 and 229 may be configured to enable sliding contact therebetween as the orthopedic fastener 32*e* and profiled washer 228 are drawn together during implantation. The sliding engagement can enable the orthopedic fastener 32*e* and profiled washer 228 combination to comply with the angle between the surface of the bone and the axis of the bore 138, as depicted at FIG. 28. The spherical profiles 227 and 227' are examples of slideably engaging surfaces that enable alignment, but the convex and concave surfaces 227 and 229 are not limited thereto. Other combinations of surface profiles may enable compliance between the orthopedic fastener 32*e* and profiled washer 228, and may include features (not depicted) that facilitate seating or gripping between the convex and concave surfaces 227 and 229.

The orthopedic fastener 32*e* is depicted as having the reduced diameter D3, the functionality of which is included with the description attendant to FIG. 15. Optionally, the orthopedic fastener 32*e* may include a threaded mid-portion 44, akin to fastener 32*c*, instead of the reduced diameter D3.

Figure 17:
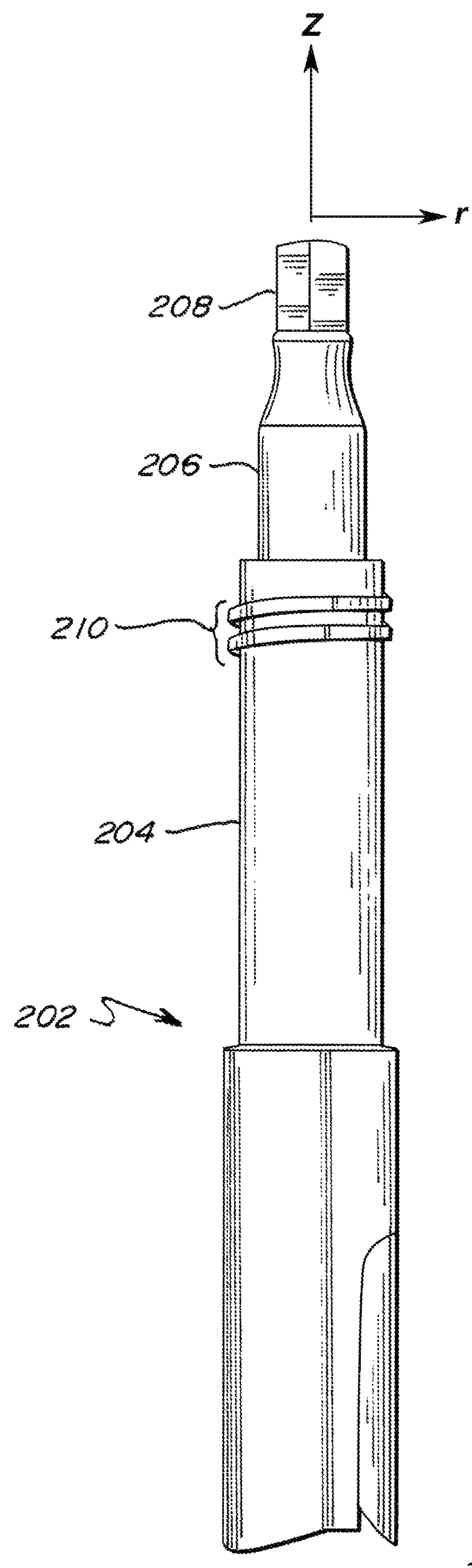
FIG. 17 is an enlarged, partial perspective view of a driver assembly for driving the orthopedic fasteners of FIGS. 14 through 16 according to an embodiment of the disclosure.

Referring to FIG. 17, a driver assembly 202 for driving the orthopedic fastener 32*c* is depicted according to an embodiment of the disclosure. The driver assembly 202 includes a sleeve 204 through which a drive shaft 206 can be axially translated. A distal end of the drive shaft defines a polygonal drive bit 208 that is configured to mate with one or both of the sequential sockets 194 of the orthopedic fastener 32*c*. In the depicted embodiment, the polygonal drive bit 208 is square-shaped, for mating with the proximal socket 194*a*. In some embodiments, the sleeve 204 includes retention threads 210 configured to threadably engage the threads 185 of the bottom-tapped hole 184.

In operation, the retention threads 210 of the sleeve 204 are threaded into the bottom-tapped hole 184 and the polygonal drive bit 208 of the drive shaft 206 inserted into and mated with one or both of the sequential sockets 194 of the orthopedic fastener 32*c*. The retention threads 210 assure that the orthopedic fastener 32*c* and the driver assembly 202 remain engaged during formation of the bore 138. The seated drive bit enables rotation of the orthopedic fastener 32*c* in both rotational directions and without binding the retention threads 210 within the bottom-tapped hole 184.

Referring to FIGS. 18 and 18A, the mounting receiver 34*c* is described in further detail according to an embodiment of the disclosure. In the depicted embodiment, the standoff 73 includes the ball pivot 82 is joined to the receiver body 72 via the standoff 73. The standoff 73 extends from a first side 252 of the ball pivot 82. A socket 248 may be defined at a second side 246 of the ball pivot 82, the second side 246 being diametrically opposed to the first side 252 along the standoff axis 74. The receiver body 72 defines the mounting aperture 62 and threads 66 concentric about the mounting axis 64. The mounting axis 64 may be substantially orthogonal to the standoff axis 74. The female threads 66 of the mounting aperture 62 may be tapered threads 262, akin to a pipe tap or a STOVER nut.

The receiver body 72 includes a first lateral face 282 and a second lateral face 284. In some embodiments, the receiver body 72 defines a wedge-shaped profile 286, with the first lateral face 282 defining a first acute angle θ1 relative to the standoff axis 74 and the second lateral face 284 defining a second acute angle θ2 relative to the standoff axis 74. In some embodiments, the wedge-shaped profile 286 is asymmetrical; that is, the first angle θ1 may be different than the second angle θ2. In some embodiments, the first angle θ1 is less than the second angle θ2.

Figure 19:
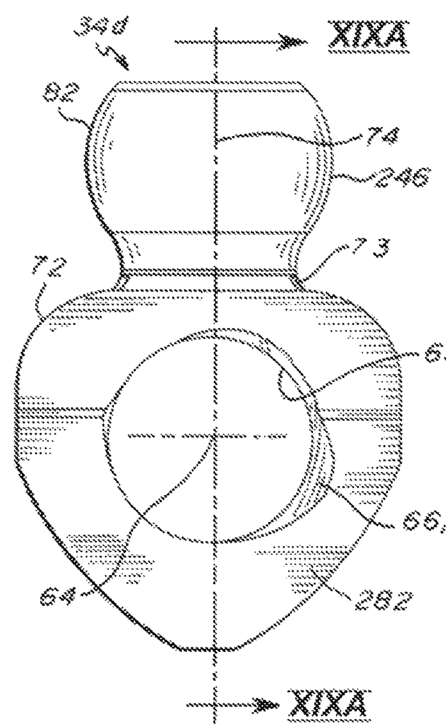
FIG. 19 is an elevational view of a mounting receiver for an anchoring system of FIG. 13 according to an embodiment of the disclosure.
Figure 19A:
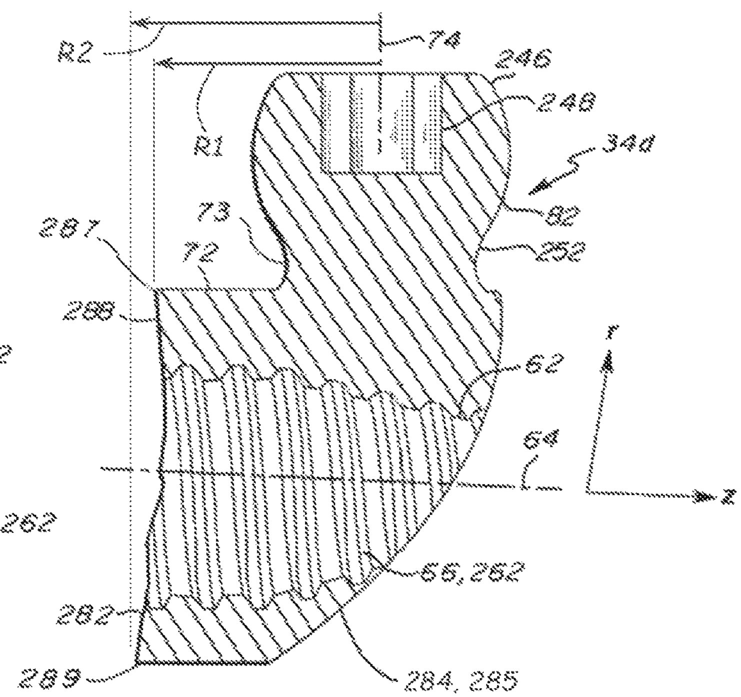
FIG. 19A is a sectional view of the mounting receiver at plane XIXA-XIXA of FIG. 19 according to an embodiment of the disclosure.
Figure 23:
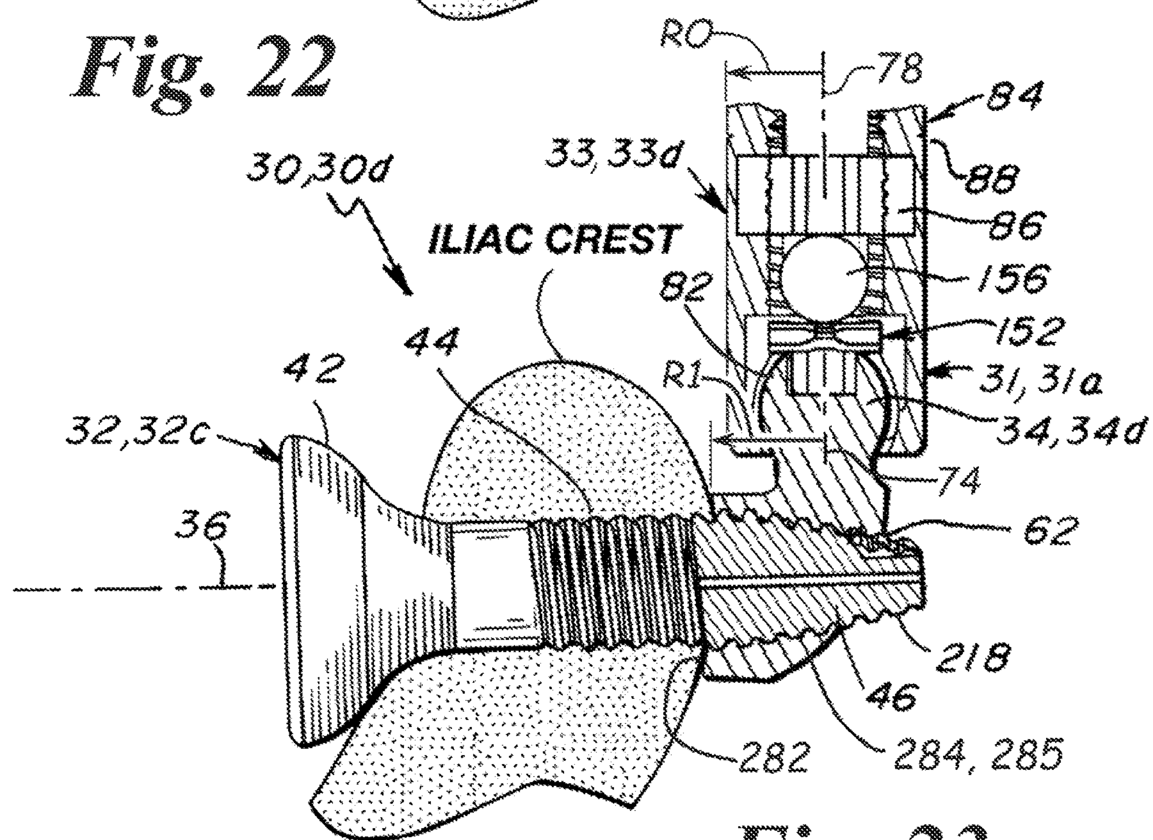

Referring to FIGS. 19 and 19A, a mounting receiver 34*d* is depicted according to an embodiment of the disclosure. The mounting receiver 34*d* may be used as an alternative to the mounting receiver 34*c* for configuration of a receiver assembly 33*d*, as depicted at FIG. 13, and includes some of the same components and attributes as the mounting receiver 34*c*, some of which are indicated with same-labeled reference characters. The first lateral face 282 of the mounting receiver 34*d* defines a concavity 288 that extends between first and second opposed lateral edges 287 and 289, the first lateral edge 287 being proximate the standoff 73. A first radial offset distance R1 is defined from the standoff axis 74 to the first lateral edge 287 at a mid-plane XIXA-XIXA, the mid-plane XIXA-XIXA being coplanar with the mounting axis 64. A second radial offset distance R2 is defined from the standoff axis 74 to the second lateral edge 289 at the mid-plane XIXA-XIXA, the second radial offset distance R2 being greater than the first radial offset distance R1. The radial offset distance R1 is greater than the outer radius RO of the tulip 31 (FIG. 23). In the depicted embodiment, the second lateral face 284 defines a convex profile 285 at the mid-plane XIXA-XIXA. The shape of the receiver body 72 of the mounting receiver 34*d* may, in some instances, allow for more lead-in or female tapered threads 262 for engagement with the threaded portion 214 of the orthopedic fastener 32*c*.

Referring to FIGS. 20 and 20A, the ball retainer 152 is depicted in greater detail according to an embodiment of the disclosure. The ball retainer 152 includes a plurality of petals 292 that extend from a flange 294. Assembly and operation of the ball retainer 152 is described, for example, at U.S. Pat. No. 10,070,895 to Barra, et al., the contents of which are hereby incorporated by reference herein in its entirety except for patent claims and express definitions contained therein. The ball retainer 152 may include a threaded aperture 296 that passes through the center of the flange 294.

Figure 24:
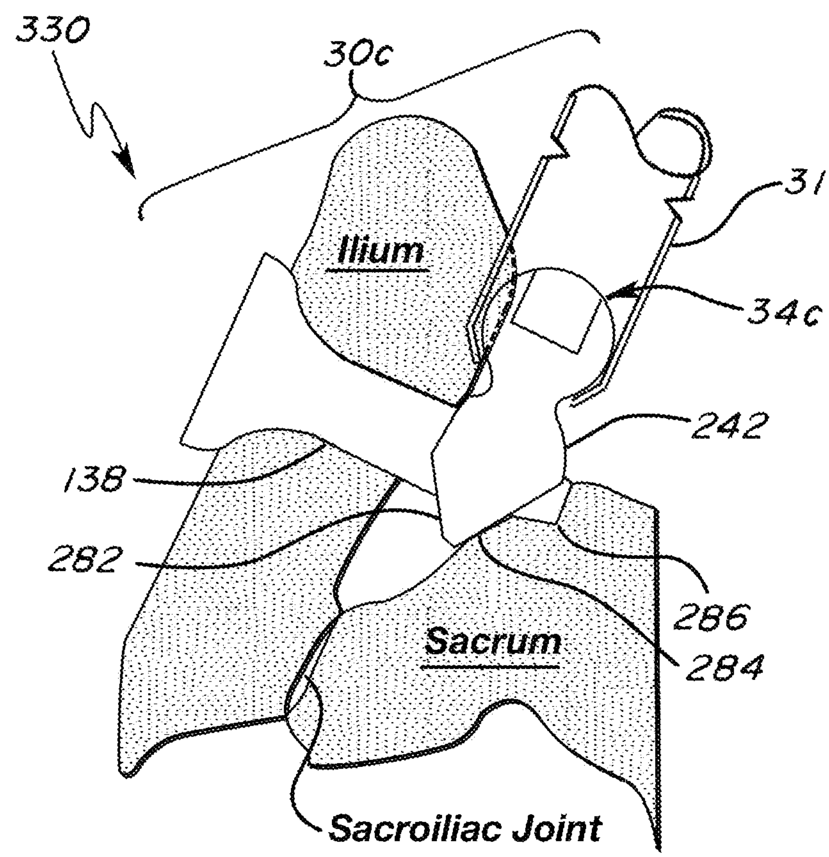
FIG. 24 is an axial, sectional view of an implanted orthopedic anchoring system according to an embodiment of the disclosure.

Functionally, the tapered female threads 262 of the receiver body 72 receives the male threads 217 of the tapered distal tip portion 218 of the orthopedic fastener 32*c*. The angled arrangement of the lateral faces 282 and 284 of mounting receiver 34*c* may conform approximately to the surfaces of the ilium and the sacrum, as depicted at FIG. 24. For mounting receiver 34*d*, the concavity 288 may act to seat the opposed lateral edges 287 and 289 onto the bone. For some implantations, the concavity 288 may conform approximately to the local surface of the ilium in certain locations.

The tapered female threads 262 and the male threads 217 of the tapered distal tip portion 218 are deformed as the orthopedic fastener 32*c* is driven into the mounting aperture 62 of the mounting receiver 34*c*, 34*d*. In some embodiments, the deformation may occur in one or more additional or alternative ways. For example, the pitch of the female threads 262 of the receiver body 72 differ from the pitch of the tapered distal tip portion 218 of the orthopedic fastener 32*c*. In another example, the cross section of the female threads 66, 262 of the receiver body 72 may be non-circular (e.g., oblong or oval), thereby and causing an interference fit at the minor diameter thereof. In yet another example, the diameter of the female threads 262 of the receiver body 72 may be less than that of the male threads 217 so as to cause an interference fit diametrically. These examples are non-limiting, and may be used in combination. The deformation of the tapered female threads 262 and the male threads 217 lock the orthopedic fastener 32*c* and the mounting receiver 34*c*, 34*d* in a fixed relationship and maintains the orthopedic fastener 32*c* in tension to secure the orthopedic anchoring system 30*d* to the ilium.

The socket 248 of the ball pivot 82 enables control of the rotational position of the mounting receiver 34*c*, 34*d* during implantation. The socket 248 is configured to accept a driver 232, such as a hex driver (depicted). The sequential sockets 194 enables the orthopedic fastener 32*c* to be driven with two different drivers (not depicted)—a square driver or a hex driver. The ball retainer 152 grips and retains the ball pivot 82 within the tulip 31*b*. The threaded aperture 294 may provide utility during assembly with the tulip 31*b*, and can also be used with a male threaded member (not depicted) for disassembly by pushing the ball pivot 82 from the tulip 31*b* with the male threaded member. The central through-passage 92 enables the orthopedic fastener 32*c* to be positioned with a guide wire 324. The self-tapping flutes 222 enable the orthopedic fastener 72 to bore through the ilium without need for pre-drilling. The radiused shoulder 182 of the distal face 178 of the head portion 128 of the orthopedic fastener 32*c* augments dilation of soft tissue as the head portion 128 passes therethrough.

Figure 21:
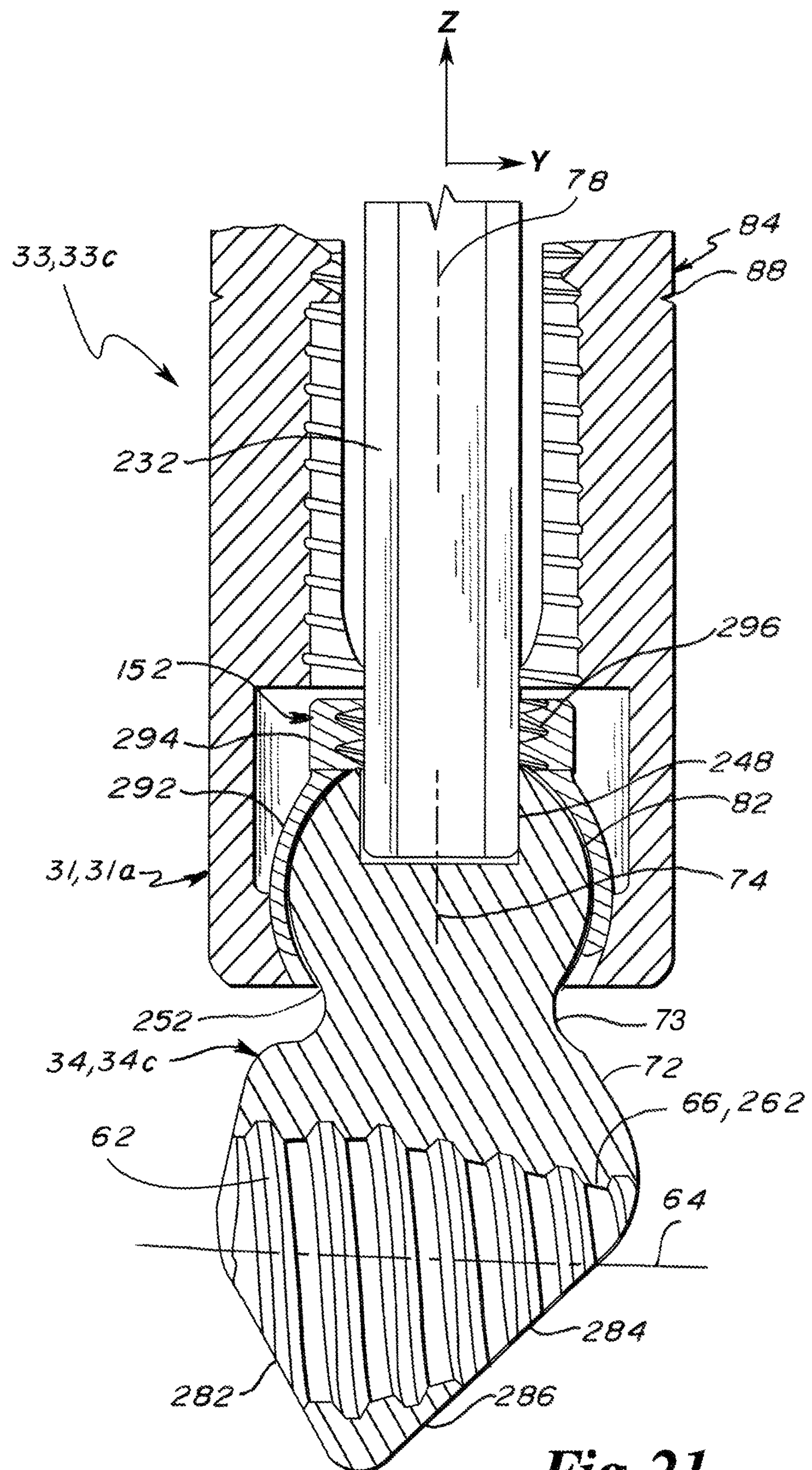
FIG. 21 is an enlarged, partial sectional view of an anchoring system of FIG. 13 assembled with a tool for orienting the receiver according to an embodiment of the disclosure.
Figure 22:
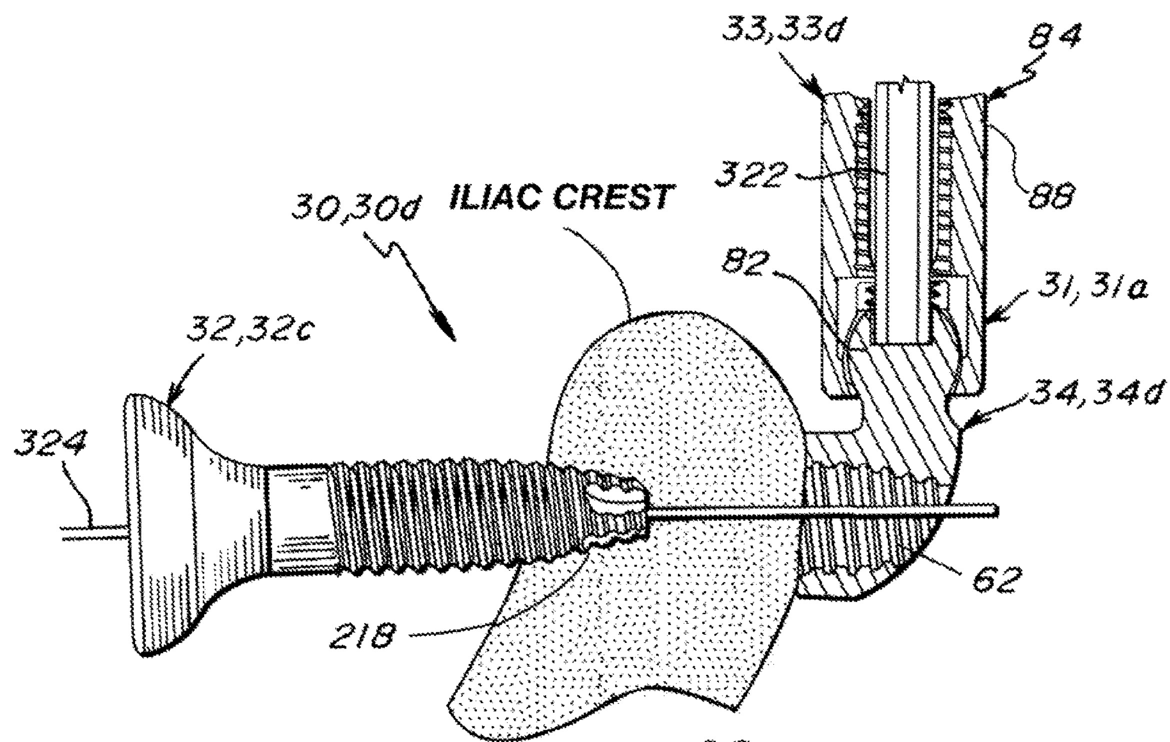
FIGS. 22 and 23 are partial sectional views of an implantation of an anchoring system of FIG. 13 according to an embodiment of the disclosure.
Figure 27:
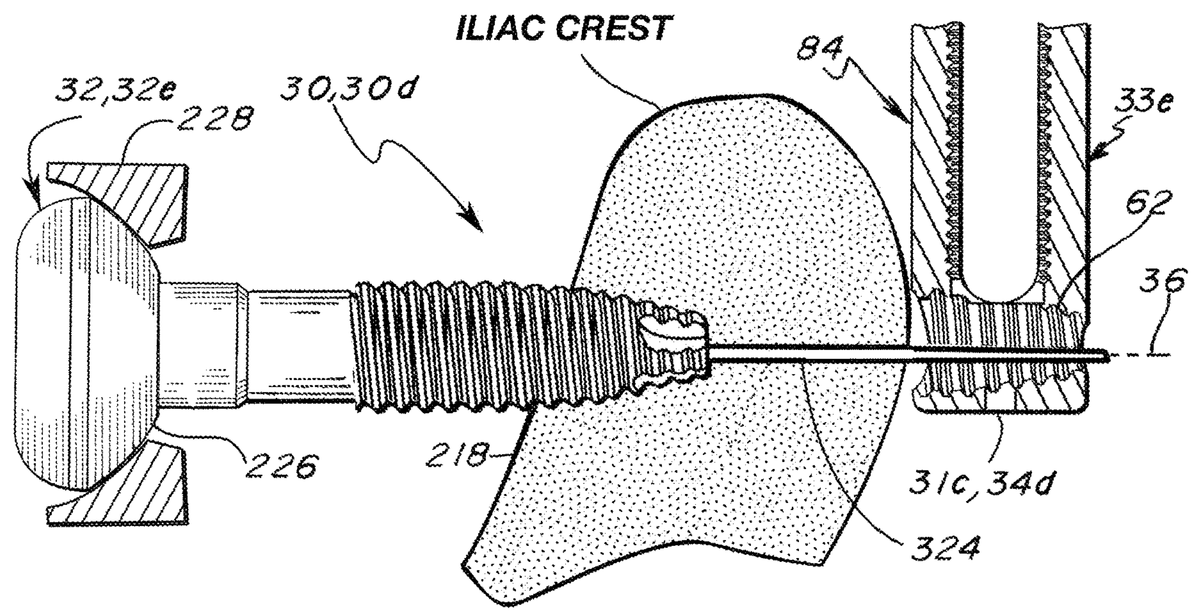
FIGS. 27 and 28 are partial sectional views of an implantation of the anchoring system of FIG. 25 according to an embodiment of the disclosure.

Referring to FIGS. 21 through 23, implantation of the orthopedic anchoring system 30*c* is depicted according to an embodiment of the disclosure. Though the specific orthopedic fastener 32*c* is represented in FIGS. 27 and 28, orthopedic fasteners 32*d* or 32*e* may also be implemented in the implantation. To implant the orthopedic anchoring system 30*c*, a posterior incision is made that extends over the iliac crest. A tool 322 (e.g., a hex wrench) is inserted through the guide tower 84, the ball retainer 152, and into the socket 248, and the assembly inserted into the posterior incision so that the lateral face 282 is proximate the surface of the ilium. A lateral incision is made that enables alignment of the orthopedic fastener 32*c* along the mounting axis 64 through the iliac crest. Using standard visualization techniques (e.g., x-ray imaging), a pilot hole is formed with a pilot hole drill (not depicted) that is passed through the ilium, for example a JAMSHIDI™ needle. Though the mounting receiver 34*d* of FIGS. 19 and 19A is depicted in FIGS. 21 through 23, the mounting receiver 34*c* of FIGS. 18 and 18A may also be implemented.

The guide wire 324 is inserted through the pilot hole and into the mounting aperture 62 of the mounting receiver 34*c*, 34*d*. The orthopedic fastener 32*c* is driven into the iliac crest with driver assembly 202. Using the tool 322 to maintain the orientation of the mounting receiver 34*c*, 34*d*, the orthopedic fastener 32*c* is bored through the ilium and into the mounting aperture 62 of the mounting receiver 34*c*, 34*d* to engage the tapered female threads 262. The orthopedic fastener 32*c* can be rotated within the bore 138 formed through the wing of the ilium by the orthopedic fastener 32*c*, drawing the receiver 34*c*, 34*d* into place, seated against the ilium. The deformation of the tapered female threads 262 and the male threads 217 of the tapered distal tip portion 218 locks the orthopedic fastener 32*c* and the mounting receiver 34*c*, 34*d* together and maintains the orthopedic fastener 32*c* in tension to secure the orthopedic anchoring system 30*d* to the ilium. The tool 322 may be withdrawn and the spinal support rod 35 clamped against the ball pivot 82 with the set screw 86 to set the tulip 31*b* in a desired orientation on the ball pivot 82 (FIG. 23).

Referring to FIG. 24, the orthopedic anchoring system 30*c* is depicted in an implanted configuration 330 according to an embodiment of the disclosure. Methods and procedures for implementing the implanted configuration 330 may be the same as depicted and described attendant to FIGS. 22 and 23 for the orthopedic anchoring system 30*c*, mutatis mutandas for the wedge-shaped profile 286 of the receiver body 72 of the mounting receiver 34*c* and the posterolateral approach to achieve the orientation depicted in FIG. 24. The implanted configuration 330 depicts the utility of the wedge-shaped profile 286 of the receiver body 72 for the mounting receiver 34*c*. The angled arrangement of the lateral faces 282 and 284 of the wedge-shaped profile 286 can conform approximately to the surfaces of the ilium and the sacrum, and may also enable passage of the mounting receiver 34*c* to the implant site with less trauma to surrounding tissue and ligaments.

Figure 25:
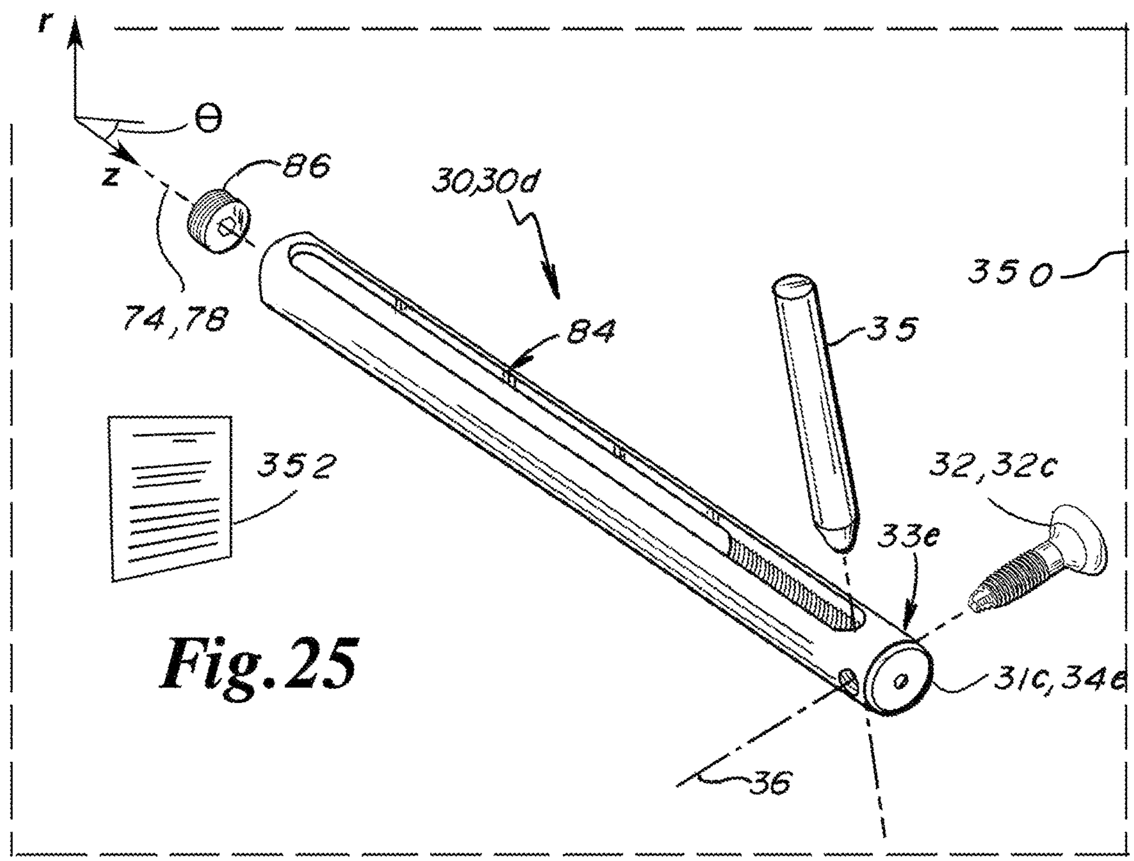
FIG. 25 is an exploded view of an anchoring system according to an embodiment of the disclosure.

Referring to FIG. 25, an orthopedic anchoring system 30*d* is depicted according to an embodiment of the disclosure. The orthopedic anchoring system 30*d* includes a receiver assembly 33*e* comprising a tulip 31*c* and a mounting receiver 34*e*. As depicted in FIG. 25, the orthopedic anchoring system 30*d* includes the orthopedic fastener 32*c*; however, any of the orthopedic fasteners 32*c*, 32*d*, or 32*e* as depicted and described herein may be implemented with the orthopedic anchoring system 30*e*. In the depicted embodiment, the orthopedic anchoring system 30*d* includes the guide tower 84 and the set screw 86. The spinal support rod 35 is also represented in line for insertion into the tulip 31*c*.

Figure 26:
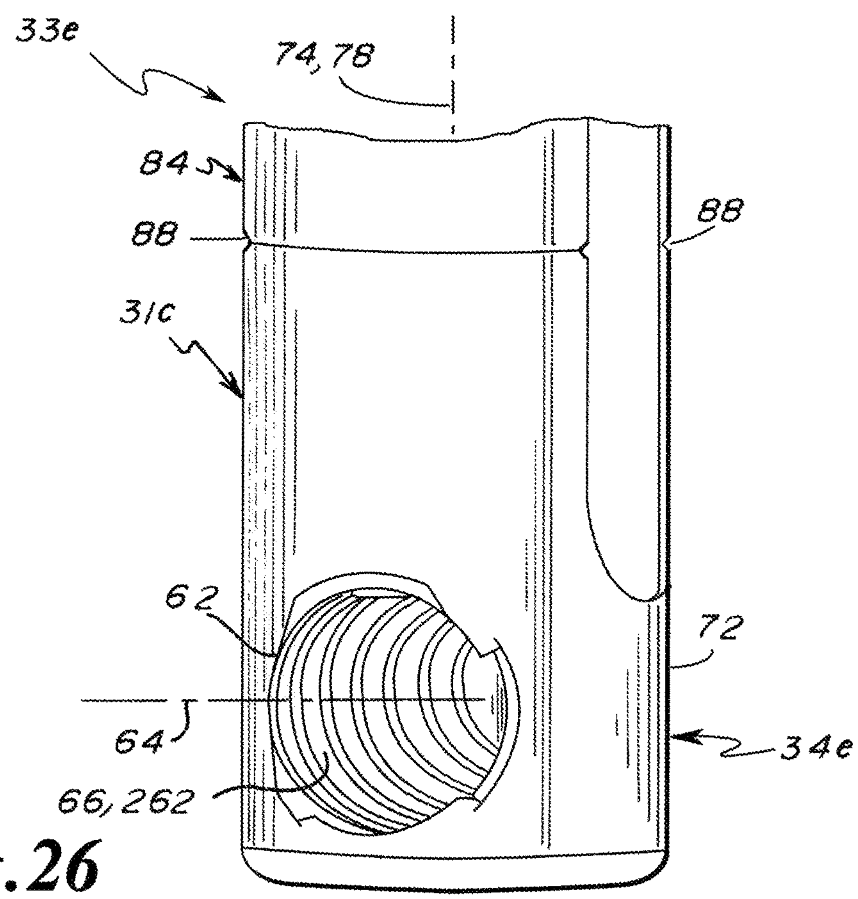
FIG. 26 is an enlarged, partial perspective view of a guide tower and tulip of the anchoring system of FIG. 25 according to an embodiment of the disclosure.

Referring to FIG. 26, the tulip 31*c* and receiver assembly 33*e* are depicted in greater detail according to an embodiment of the disclosure. The receiver assembly 33*e* includes the mounting receiver 34*e* and tulip 31*c* as an integrated or unitary structure. The mounting aperture 62 of the mounting receiver 34*d* may include the same components and attributes as the mounting aperture 62 of the mounting receiver 34*c*, 34*d*, some of which are indicated in with same-labeled reference characters. During implantation, the tapered female threads 262 mate with the male threads 217 of the tapered distal tip portion 218 of the orthopedic fasteners 32*c*, 32*d* as previously described. Though not depicted, it is also contemplated that the tulip 31*c* be configured to have the same profile characteristics as the wedge-shaped profile 286 of the mounting receiver 34*c* or the concavity 288 of the mounting receiver 34*d*.

Referring to FIGS. 27 and 28, implantation of the orthopedic anchoring system 30*d* is depicted according to an embodiment of the disclosure. Though the orthopedic fastener 32*e* is represented in FIGS. 27 and 28, orthopedic fasteners 32*c* or 32*d* may also be implemented in the implantation. To implant the orthopedic anchoring system 30*d* as depicted, a posterior incision is made that extends over the iliac crest. The guide tower 84 and receiver assembly 33*d* are inserted into the posterior incision so that the tulip 31*c* is at the desired location adjacent the ilium. The mounting aperture 62 is oriented to receive the orthopedic fastener 32*d* through the ilium using the guide tower 84 to control the tulip 31*c*. A lateral incision is made that enables alignment of the orthopedic fastener 32*d* along the mounting axis 64 through the ilium. Using standard visualization techniques (e.g., x-ray imaging), a pilot hole is formed with a pilot hole drill (not depicted) that is passed through the ilium, for example a JAMSHIDI™ needle.

The guide wire 324 is inserted through the pilot hole and into the mounting aperture 62 of the tulip 31*c*. The orthopedic fastener 32*d* is driven into the ilium with the driver assembly 202. Using the guide tower 84 to maintain the orientation of the tulip 31*c*, the orthopedic fastener 32*d* is bored through the ilium and into the mounting aperture 62 of the tulip 31*c* to engage the tapered female threads 262. After the bore 138 is formed, the orthopedic fastener 32*d* can be rotated within the bore 138, thereby drawing the mounting receiver 34*e* into seating contact against the ilium. The deformation of the tapered female threads 262 and the male threads 217 of the tapered distal tip portion 218 locks the orthopedic fastener 32*d* and the mounting receiver 34*d* together. The tulip 31*c* may be positioned in an angular orientation about the rotation axis 36 in a monoaxial arrangement as the orthopedic fastener 32*d* is set within the tulip 31*c*. The spinal support rod 35 clamped against the orthopedic fastener 32*d* with the set screw 86 (FIG. 28) to set the tulip 31*c* in a desired orientation about the central rotation axis 36.

In some embodiments, some or all of the components of the orthopedic anchoring systems 30 are provided as a kit 350 (depicted at FIGS. 13 and 25), complete with instructions 352 for use. The instructions 352 are provided on a tangible, non-transitory medium, and may be physically included with the kit 350 such as on a printed document (depicted), compact disc, or flash drive. Non-limiting examples of a tangible, non-transitory medium include a paper document and computer-readable media including compact disc and magnetic storage devices (e.g., hard disk, flash drive, cartridge, floppy drive). The computer-readable media may be local or accessible over the internet. The instructions 352 may be complete on a single medium, or divided among two or more media. For example, some of the instructions 352 may be written on a paper document that instruct the user to access one or more of the steps of the method over the internet, the internet-accessible steps being stored on a computer-readable medium or media. The instructions 352 may embody the techniques and methods depicted or described herein using text, photos, videos, or a combination thereof to instruct and guide the user. The instructions may be in the form of written words, figures, photos, video presentations, or a combination thereof to instruct and guide the user.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment (s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. An anchoring system for a spinal support assembly, comprising:

an orthopedic fastener including a proximal end portion, a mid-portion, and a threaded distal end portion arranged along a central axis, said proximal end portion including a head portion;

a mounting receiver defining a mounting aperture configured to threadably engage said threaded distal end portion of said orthopedic fastener along a receiver axis, said mounting aperture being accessible from a first lateral face of said mounting receiver that faces said head portion of said orthopedic fastener when said mounting aperture is threadably engaged with said distal end portion of said orthopedic fastener, said mounting receiver including a standoff that defines a standoff axis, said standoff axis extending radially outward relative to said receiver axis, said first lateral face being located at a radial offset distance relative to said standoff axis, said central axis and said receiver axis being concentric when said orthopedic fastener and said mounting receiver are engaged; and a support rod receptacle coupled to said standoff of said mounting receiver, said support rod receptacle extending radially outward relative to said receiver axis and defining a support rod receptacle axis and an outer radius about said support rod receptacle axis, wherein said head of said orthopedic fastener and said first lateral face of said mounting receiver are configured for registration against bone when said mounting aperture is threadably engaged with said distal end portion of said orthopedic fastener, and wherein said outer radius of said support rod receptacle is less than said radial offset distance of said first lateral face.

2. The anchoring system of claim 1, wherein said first lateral face extends between a first lateral edge and a second lateral edge, said first lateral edge being proximate said standoff and located at a first radial offset distance relative to said standoff axis, said second lateral edge being located at a second radial offset distance relative to said standoff axis, said second radial offset distance being greater than said first radial offset distance.

3. The anchoring system of claim 2, wherein said standoff includes a ball pivot, said support rod receptacle being configured to receive said ball pivot to define a polyaxial connection.

4. The anchoring system of claim 3, comprising a ball retainer, said ball pivot being secured to said support rod receptacle with said ball retainer.

5. The anchoring system of claim 1, wherein said mounting receiver includes a second lateral face opposite said first lateral face, said second lateral face defining a convex profile.

6. The anchoring system of claim 1, wherein said first lateral face of said mounting receiver defines a concave face.

7. The anchoring system of claim 1, wherein the threads of said mounting aperture are tapered.

8. The anchoring system of claim 1, wherein said bone is an ilium.

9. The anchoring system of claim 1, wherein the threads of said threaded distal end portion of said orthopedic fastener are male.

10. The anchoring system of claim 1, wherein said orthopedic fastener is self-tapping.

11. The anchoring system of claim 1, wherein said orthopedic fastener defines a central passage configured for passage of a guide wire.

12. The anchoring system of claim 1, wherein said head portion includes a flange having a distal face that includes a radiused shoulder.

13. The anchoring system of claim 1, wherein said head portion defines a bottom-tapped hole accessible from a proximal face of said head portion.

14. The anchoring system of claim 1, wherein said proximal end portion defines a first polygonal socket that extends distal to and is accessible from a bottom-tapped hole.

15. The anchoring system of claim 1, comprising a profiled washer that surrounds said proximal end portion of said orthopedic fastener.

16. The anchoring system of claim 15, wherein said orthopedic fastener includes a head portion at said proximal end portion, said head portion being configured to engage a concave face of said profiled washer.

17. The anchoring system of claim 16, wherein:

said concave face of said profiled washer defines a spherical profile; and said head portion defines a convex spherical profile that interfaces with said concave spherical profile of said profiled washer.

18. An anchoring system for a spinal support assembly, comprising:

an orthopedic fastener including a proximal end portion, a mid-portion, and a threaded distal end portion arranged along a central axis, said proximal end portion including a head portion;

a mounting receiver defining a mounting aperture configured to threadably engage said threaded distal end portion of said orthopedic fastener along a receiver axis, said mounting aperture being accessible from a first lateral face of said mounting receiver that faces said head portion of said orthopedic fastener when said mounting aperture is threadably engaged with said threaded distal end portion of said orthopedic fastener;

a support rod receptacle coupled to said mounting receiver and extending radially outward relative to said receiver axis, wherein said head portion of said orthopedic fastener and said first lateral face of said mounting receiver are configured to clamp said anchoring system to an ilium through which said mid-portion of said orthopedic fastener passes when said anchoring system is implanted.

19. The anchoring system of claim 18, wherein:

said mounting receiver includes a standoff to which said support rod receptacle is coupled, said standoff defining a standoff axis that extends radially outward relative to said receiver axis, said first lateral face of said mounting receiver being located at a radial offset distance relative to said standoff axis; and said support rod receptacle defines an outer radius about a support rod receptacle axis, said outer radius of said support rod receptacle being less than said radial offset distance of said first lateral face.

* * * * *